(12) United States Patent
Pompon et al.

(10) Patent No.: US 7,294,460 B2
(45) Date of Patent: Nov. 13, 2007

(54) SUPPORTED DOUBLE LAYER STRUCTURE FOR DISPLAYING A NUCLEIC ACID ASSOCIATED WITH A PROTEIN

(75) Inventors: Denis Pompon, Gif sur Yvette (FR); Wilfrid Boireau, St Arnoult En Yveline (FR); Marie-Agnès Sari, Paris (FR); Sophie Bombard, Savigny sur Orge (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 439 days.

(21) Appl. No.: 10/474,299

(22) PCT Filed: Apr. 3, 2002

(86) PCT No.: PCT/FR02/01150

§ 371 (c)(1), (2), (4) Date: Apr. 22, 2004

(87) PCT Pub. No.: WO02/081740

PCT Pub. Date: Oct. 17, 2002

(65) Prior Publication Data

US 2006/0110728 A1 May 25, 2006

(30) Foreign Application Priority Data

Apr. 4, 2001 (FR) .................................. 01 04559

(51) Int. Cl.
*C12Q 1/68* (2006.01)
*C12M 1/00* (2006.01)

(52) U.S. Cl. ........................................ 435/6; 435/283.1

(58) Field of Classification Search ............... 435/6, 435/283.1
See application file for complete search history.

(56) References Cited

FOREIGN PATENT DOCUMENTS

WO        WO 01/20330        3/2001

OTHER PUBLICATIONS

Caide et al. Numerical simulations of Surface Plasmon Resonance System for monitoring DNA hybridizations and detecting protein-lipid film interactions. European Biophysics Journal 28: 151-157 (1999).*
Lucas et al. Detection of DNA via an Ion Channel Switch Biosensor. Analytical Biochemisrtry 282 : 70-79 (Jun. 2000).*
Cremer et al. Creating spatially addressed arrays of planar supported fluid phospholipid membranes. Journal of the American Chemical Society 121: 8130-8131 (1999).*
Boireau et al. BioEngineering and chartacterization of DNA-protein assemblies floating on supported membranes. Biotechnology and Bioengineering 72(2) : 225-231 (Published Online Dec. 5, 2001 and in Print Jan. 20, 2002).*
"Numerical simulations of surface plasmon resonance system for monitoring DNA hybridization and detecting protein-lipid film interactions", Xiao Caide, et al., European Biophysics Journal, vol. 28, No. 2, pp. 151-157.

* cited by examiner

*Primary Examiner*—Ethan Whisenant
(74) *Attorney, Agent, or Firm*—Blakely Sokoloff Taylor & Zafman

(57) ABSTRACT

The invention concerns novel biosensors, in particular a support for displaying nucleic acids and for detecting both the presence of nucleic acids in a sample and the linkage between proteins and nucleic acids, as well as the linkage between a ligand and a protein linked to a nucleic acid.

31 Claims, 11 Drawing Sheets

SUPPORTED DOUBLE LAYER STRUCTURE FOR DISPLAYING A NUCLEIC ACID ASSOCIATED WITH A PROTEIN

The present patent application is a non-provisional application of International Application No. PCT/FR02/01150, filed Apr. 3, 2002.

The present invention relates to novel biostructures which can in particular be used as biosensors, in particular a support for displaying nucleic acids and for detecting both the presence of nucleic acids in a sample and the interaction between proteins and said nucleic acids, and also the binding between a ligand and a protein linked to a nucleic acid.

The development of DNA biosensors, also referred to as DNA chips, has considerably increased over the last few years. The impact of such biosensors has mainly been directed toward sequencing, gene expression mapping, diagnosis (detection, damage, mutation, etc.) and analysis of DNA-ligand interactions (hybridization, etc.). Most of the biosensors employed use techniques for immobilizing single-stranded nucleic acid, or ssDNA, molecules, the analysis being carried out by virtue of optical transduction, electrochemical or piezoacoustic systems.

The fact that biological membranes are highly important in physiological terms as a site for numerous chemical and metabolic reactions has led to a craze for developing lipid models on inorganic surfaces. The design of such biocompatible and biofunctional structures on solid substrates has made it possible to develop models involving interdisciplinary fields which have brought about an expansion of many lines of scientific research and also practical applications. The main applications have thus concerned:

the production of matrices for immobilizing enzymes, cell receptors or hormones in nondenaturing environments,
the design of interfaces for capturing cells in order to study the effects of pharmaceutical molecules on the outcome of the cell,
the self-assembly of very resistant membranes for the development of biosensors.

The analytical methods applied to the analysis of DNA-DNA biomolecular interactions, such as they are represented at the heart of DNA chip devices, are essentially based on the attachment of a single-stranded DNA (ssDNA) within a delimited area on a substrate. The main techniques for producing DNAs covalently attached to the substrate are the in situ synthesis of ssDNA on the support, the assembly of ssDNAs which have been chemically modified to allow grafting onto the support, or microdeposition onto an adsorbent matrix (Boncheva et al., 1999, Berney et al., 2000, Wittung-Stafshede P. et al., 2000). Now, in the development of biosensors, the arrangement of biomolecules at the interfaces plays a crucial role. In order to obtain highly sensitive surfaces, it is important to exhibit receptor molecules in such a way that the corresponding ligand can interact without steric hindrances. However, in these various approaches, the means used to produce these DNA matrices generate artifacts (errors in the in situ syntheses or in functionalization of oligonucleotides) which cause nonspecific adsorptions; thus, some of the current studies relate to means for getting round these various limitations (Steel et al., 2000).

Another limitation of these systems is inherent to the method of displaying the ssDNAs. The highly compacted nature of the molecules on the surface leads to the appearance of steric constraints which affect the hybridization efficiency of the chip. While the immobilization of ssDNAs on a surface is to date the most commonly used alternative, it also constitutes that which restricts the geometry of the device, resulting in a complete loss of flexibility and of modularity of the assembly.

One of the characteristics of the present invention is to provide a novel method of displaying nucleic acids at the surface of the substrate. The method of displaying the nucleic acids according to the invention is original in that it allows the nucleic acids to be mobile, and thus makes it possible to detect any change in the state of said nucleic acids by detecting a transition between two states exhibiting distinct organizational levels.

Thus, the subject of the present invention is a cell for displaying a nucleic acid, comprising:

a support which is substantially flat on an atomic scale,
a protein III having an unequivocal three-dimensional structure (stable and defined spatial organization),
a nucleic acid IV linked to said protein III, the nucleic acid-protein assembly being laterally mobile relative to said support, such that the hybridization of a target nucleic acid to said nucleic acid IV or the change in conformation of said nucleic acid IV can be or is detected via the geometric reorganization of the nucleic acid-protein assembly.

In a preferred case of the present invention, said protein III is chosen from the group consisting of proteins having a redox center and proteins having an anisotropic optical absorption property. The protein III will be described in greater detail later.

The term "cell" is intended to mean a laterally delimited subset of the surface, which is characterized by a structural homogeneity, and many identical or variant copies of which can be reproduced on the inorganic support.

A cell can in particular be used for detecting a specific type of nucleic acid (as will be seen later), different from the nucleic acid detected by using another cell.

It is understood that the present invention also relates to a support displaying a plurality of cells according to the invention.

In the present application, the term "floater" may be used to denote the assembly consisting of the protein which is mobile relative to the support, attached to the oligonucleotide.

The oligonucleotide linked to the floater may be referred to as "primer" in the present application.

The following abbreviations may also be used in the present application:
DMPC: dimyristoylphosphatidylcholine
DOGS: 1,2-dioleoyl-sn-glycero-3-[(N-(5-amino-1-carboxypentyl)iminodiacetic acid)succinyl]
DOPC: dioleoyl phosphatidylcholine
DPDPB: 1,4-di-[3'-(2'-pyridyldithio)propionamido]butane
DPPC: dipalmitoyl phosphatidylcholine
dsDNA: double-stranded DNA
DTT: dithiothreitol
Hb5(His)4: human cytochrome b5-histidine 4 fusion protein
Hb5(His)4mut24: cysteine (position 24) mutant of Hb5 (His)4
MIAC: metal ion affinity chromatography
OG: octyl glucopyranoside
OM: octadecyl mercaptan
SPR: surface plasmon resonance
RU: response unit
SAM: self assemblage monolayer
ssDNA: single-stranded DNA It is advantageous for the oligonucleotide not to be directly in contact with the support, thereby allowing an improved display with respect to the target nucleic acids or other elements which interact and modify the conformation of the primer.

In a particular case, the protein-nucleic acid assembly is mobile relative to the support due to the fact that the protein is itself mobile in a lipid layer which is itself attached to the support. A lipid bilayer is preferably used.

Briefly, this assembly consists of a lipid membrane reconstituted on a flat surface which is inorganic in nature. This is then referred to as a supported lipid membrane.

Such a model has properties which are close to biological membranes in terms of compactness of the elements making it up, of compartmentalization, and of fluidity of the elements making up these models and also of most of the molecules incorporated or interacting with this model (Heyse et al., 1998, Marchal et al., 1998).

This property of membrane dynamics is the reason for the lateral mobility of the proposed structures and for the reorganization allowing signal transduction and domain formation. In addition, it is possible to modulate as desired the molecular composition of this lipid structure in order to modify its intrinsic properties or to introduce new potentialities.

Thus, in a preferred embodiment, the present invention relates to a cell for displaying a nucleic acid, comprising:
  a support which is substantially flat on an atomic scale, to which is attached
  a hydrophobic monolayer I, on which is present
  a monolayer II comprising phospholipids,
  a bridging molecule having a hydrophobic end which can interact with the monolayer II, and an end which is chemically functionalized so as to form a stable bond with a protein III,
  a protein III having an unequivocal three-dimensional structure, said protein III being laterally mobile in said layer II,
  a nucleic acid IV unequivocally attached to said protein III, preferably via a molecular arm.

The fact that the protein is mobile in the layer II (lipid sheet) ensures lateral dynamics, i.e. the possibility of the floater+primer assembly diffusing freely in two dimensions in the absence of any additional geometric constraint which would be imposed by interaction of the primer with other nucleic acids. The membrane fluidity allows the reorganization and the contact of molecules essential for the self-assembly into superstructures. In addition, in some embodiments, the supramolecular assembly thus produced is characterized by a strong modularity: each step for producing or for destructuring this assembly may be carried out irreversibly by the controlled action of the solutes present in an aqueous phase or by the action of thermal conditions or of an electrostatic environment, etc.

The grafting of a single-stranded nucleic acid onto the protein has been carried out so as to use the very particular properties of these biostructures. In this way, the oligonucleotides are grafted onto blocks which are protein in nature and which are floating on the upper lipid monolayer of the membrane model.

This arrangement offers the following advantages:
  Lateral mobility of the floating protein anchor and, consequently, of the grafted ssDNA.
  Suppression of the nonspecific interactions of the ssDNAs on the flat support due to an appropriate lipid covering.
  Control of the density of the ssDNAs present at the surface of the biosensor (great modularity).
  In some embodiments, reversibility of the various supramolecular interactions via aqueous treatment procedures (allowing regeneration of the biosensor).

The terms "nucleic acid", "nucleic acid sequence", "polynucleotide", "oligonucleotide", "polynucleotide sequence" or "nucleotide sequence", terms which may be used indifferently in the present description, are intended to denote a precise series of natural or synthetic nucleotides defining a fragment or a region of a nucleic acid and which can correspond equally to a single-stranded, double-stranded or triplex DNA or RNA. Thus, the nucleic acid sequences according to the invention also encompass PNAs (peptide nucleic acids), or the like. The bonds between the various bases may be conventional phosphodiester bonds, or modified bonds such as phosphorothioates or methylphosphonates. The oligonucleotides may also be chimeric, i.e. they may have different bonds and/or bases. The term thus encompasses any variant of a nucleic acid sequence which exhibits a property of recognition by hybridization.

Preferably, the nucleic acid linked to the protein in the cell according to the invention is a single-stranded nucleic acid. Its size is not a determinant parameter according to the invention, and it can be readily chosen using the general knowledge of those skilled in the art.

In a preferred embodiment, the nucleic acid is attached to said protein via a reversible bond. This reversible bond may, moreover, be covalent. Thus, it is possible to attach the nucleic acid to the protein such that disulfide bonds are involved, which bonds can, however, be reversed in the presence of appropriate agents, or under particular conditions. Thus, the reversible bond can, in this particular case, be considered to be a bond which can be readily broken.

In one embodiment, the nucleic acid is attached to said protein via a covalent bond. Such a bond is known to those skilled in the art and can in particular be produced using modified bases in the oligonucleotide allowing coupling to a chemical arm which is functionalized so that it can be coupled specifically to the protein of the floater.

Moreover, there can be two types of grafting: a closely related grafting can be carried out so as to place the nucleic acid molecule and the protein tightly next to one another, or grafting via a molecular spacer arm can be carried out so as to provide greater conformational freedom of the DNA with respect to the floater. A spacer arm attached in an unequivocal manner to said protein is therefore preferably used. In fact, as will be developed later, it is advantageous for the geometry of the floater to be completely defined. Thus, it is preferable for the spacer arm to be attached to the protein at a precise site of said protein.

In the embodiment in which the nucleic acid and the protein are placed next to one another, said spacer arm can then be a metal complex such as cis-platinum, trans-platinum, europium or another transition metal involving ligands originating from the very structure of the nucleic acid and one or more ligands originating from the very structure of the protein III of the floater.

When the spacer arm is longer, allowing greater flexibility of the nucleic acid, a spacer arm is preferably chosen which attaches a thiol- or amino-function introduced onto the nucleic acid, in particular via a modified base (it being possible for the base chosen to be any base, i.e. it is possible to choose a base in the 3' position, in the 5' position or within the oligonucleotide, this alternative possibly having certain advantages, in particular of providing the oligonucleotide with a greater degree of freedom), to another functionality present, preferably uniquely present, on the protein. This second function is preferably also a thiol function, carried for example by a cysteine.

However, other types of grafting of a nucleic acid to a protein exist. They can in particular be grafted onto an arginine in the protein. It is, however, preferable, in order to respect a principle of the invention, for the coupling of the nucleic acid to the protein to be specific, completely defined and unequivocal in molecular terms. Thus, any type of random grafting of the nucleic acid onto the protein which may create an ambiguity or a heterogeneity in the structure of the floaters according to the invention is generally excluded.

Thus, preferably, the nucleic acid IV is attached to said protein III via a compound chosen from:
- a spacer arm connecting two identical or different, chemically reactive residues of the nucleic acid IV and of the protein III, chosen from the group consisting of thiols, amines, amides and arginines;
- a metal complex such as cis-platinum, trans-platinum, europium, or a complex of nickel, of copper or of ruthenium coordinated, firstly, with an amino residue or a group of amino residues of said protein III and, secondly, with one or more natural or modified bases of the nucleic acid IV,
- a covalent or noncovalent protein complex involving the nucleic acid IV.

The protein in the cell according to the present invention has a geometry which can be detected in an unequivocal manner, i.e. a stable and defined spatial organization. This means in particular that its conformation in the cell according to the present invention is identical whatever the protein observed, when the cell according to the invention displays several identical floaters. This also means that bringing the cell into contact with outside nucleic acids capable of interacting with the primers in an unequivocal manner will lead to a highly repetitive organization of the floaters, in spatial terms, within the cell. In particular, the external nucleic acids may bring about the association of floaters in organized groups and these groups of floaters may, by virtue of their lateral mobility, interact with one another noncovalently so as to form, within each cell, a network of floaters which is highly organized in two-dimensional terms. The properties (physical, electrical, optical, quantum properties) of this highly organized network will then differ from the dynamic properties of disorganized floaters within the cell in the absence of any interaction with the external nucleic acid.

Preferably, the protein of the floater will be chosen such that the variations in spatial organization of the floaters relative to one another lead to a signal which can be detected by any method, in particular an electrical, optical or resonance method.

Proteins having this property will preferably be chosen from the group consisting of proteins having a redox center and/or an anisotropic optical absorption property and/or an intrinsic fluorescence property.

Mention is in particular made of cytochromes, and more preferably human cytochrome b5, yeast cytochrome b5 or cytochrome b5 of any other origin, flavodoxins, ferridoxins, azurins and other blue copper proteins, and multiheme proteins of the bacterial cytochrome c class, which have both a redox center and anisotropic optical absorption properties. Among the fluorescent proteins, mention will preferably be made of green fluorescent protein (GFP) and analogs thereof obtained by site-directed mutagenesis or directed evolution.

In a preferred case of implementation, said protein is water soluble. It may also have undergone modifications, some of which are indicated below, provided that these modifications result in a protein with a stable and defined three-dimensional structure satisfying the criteria as defined according to the present invention.

Thus, in a preferred embodiment, said protein has undergone a modification which has allowed the introduction of a unique site into said protein, in order to effect said bond with said nucleic acid. The fact that a unique site is introduced into the protein according to the invention, in order to graft the nucleic acid, thus makes it possible to strongly promote the unicity, the specificity and the unequivocal definition of the protein-nucleic acid bond.

In a particular case, said modification consists of a mutation of said protein so as to leave remaining or to introduce just one predetermined unique amino acid. The mutation can be introduced by mutation of the nucleic acid encoding the protein; this is the simplest method which will be favored by those skilled in the art. The unique site for grafting the nucleic acid will then be this predetermined unique amino acid. It is in fact within the scope of those skilled in the art to determine, according to the sequence of the protein which has been chosen in order to implement the invention, the amino acids to be modified so as to leave remaining just one of them, or so as to introduce one which is not present in the native protein. Thus, and in order to illustrate this fact, when the protein which is used is a cytochrome b5, it is possible to introduce a cysteine into the protein, since this amino acid is absent from the native protein.

It is, moreover, always very advantageous to modify the protein such that it has only one cysteine, or at least such that it has a unique free cysteine (not involved in a disulfide bond with another cysteine).

It is also preferable, for correct implementation of the method according to the invention, for the modification in the protein to be such that this facilitates the grafting of the nucleic acid, i.e. such that the amino acid used for said grafting is located at the periphery (at the surface) of said protein. It is within the scope of those skilled in the art to determine, as a function of the protein chosen, the best position for introducing the modification into the protein. In cytochrome b5, introduction of the cysteine by mutation of serine 24 has thus been exemplified. However, alternative positions could easily have been chosen.

Thus, according to the three-dimensional structure of a cytochrome b5 of a mammal other than human (for example rat or bovine), it is entirely possible to select the amino acids to be modified so as to introduce just one cysteine into the sequence of the protein. For example, the representation in three dimensions will make it possible to target the most peripheral amino acids of the protein, i.e. those which promote better reactivity with the modified nucleic acid. In addition, it may be of crucial advantage to link the ssDNA in the region of the redox center of the protein: a mutation of glycine 47 would make it possible to obtain such a connection.

One of the important characteristics of the present invention is that the protein III is mobile relative to the layer II of the cell according to the invention. This also ensures the mobility of the nucleic acid IV attached to the protein III in the cell, relative to the support according to the invention.

The mobility of the protein in the layer II can be obtained in various ways, in particular when said protein has a hydrophobic tail which allows it to be anchored in the layer II. The sequences of hydrophobic tails are known in the literature, and it is within the scope of those skilled in the art to choose such a sequence and to modify the selected protein by genetic engineering in order to introduce such an anchoring sequence. It is then advantageous to choose a hydrophobic tail which is short, so that it becomes anchored only in the layer II, without penetrating into the layer I. This makes it possible in particular to improve the mobility of the protein in the layer II, by reducing the "rubbing" phenomena which may be observed if the hydrophobic tail is too large. The optimization of these elements remains within the scope of those skilled in the art.

In a preferred case, however, said protein is attached to a phospholipid of the layer II and, in a particular case, to an artificial phospholipid preferably introduced in a small proportion (i.e. in a proportion less than 10%, preferably less than 5%, more preferably approximately 2%). As a result, the mobility of the protein relative to the layer II is then similar to the mobility of the phospholipids in said layer. Such a mobility is generally greater than when the protein has a hydrophobic tail. This makes it possible to improve the levels of performance of the cell according to the invention, as will be seen.

Those skilled in the art have several methods available to them for producing a protein-phospholipid bond. Mention may in particular be made, among covalent bonds, of acylation, farnesylation, the use of a GPI (glycosylphosphatidylinositol) anchoring sequence or the incorporation of a phospholipid or of a fatty acid into a specific residue of the protein III by any artificial method.

It may, however, be preferable to have a reversible bond, i.e. a bond which can be broken in the presence of reagents or under particular conditions, but which is stable under the usual working conditions or in the presence of the usual working reagents (hybridization of nucleic acids, study of binding between biological elements, etc.).

In general, those skilled in the art can use all the known methods for attaching a protein to a liposome, for example, since liposomes generally consist of phospholipids.

Thus, it is in particular possible to use an arm capable of linking a metal chelate on one side and an amino acid on the other, using, in the layer II, a modified phospholipid, said phospholipid having a chelate-binding zone.

Thus, a preferred phospholipid according to the invention is DOGS, or 1,2-dioleoyl-sn-glycero-3-[(N-(5-amino-1-carboxypentyl)iminodiacetic acid)succinyl]. This phospholipid is a synthetic phospholipid possessing an iminodiacetate residue which complexes a nickel divalent cation.

In order to promote the mobility of the protein in the layer II, it is advantageous to choose the phospholipids of said layer II so that they have hydrophobic tails chosen such that said layer is not in the crystalline state, but in the fluid state at the temperature for use.

These properties of fluidity of a phospholipid layer are known to those skilled in the art, and there are in particular diagrams for choosing the chain length and the unsaturation in order to obtain fluidity at the temperature for use (Gulik-Krzywicki et al., 1967).

This temperature for use obviously depends on the use for which the sensor is intended. Thus, when hybridization is sought, the temperature for use may be different from that used when the binding of a protein to a nucleic acid is studied. Furthermore, transition between fluid and gel states may be strategic in the context of a detection technique based on super-structure imaging, such as atomic force microscopy (AFM).

Those skilled in the art will seek the phospholipids most suitable for the layer II as a function of the temperature for use. As a general rule, and in order to simplify and improve the potentialities of the biosensor, fluidity of the layer II at ambient temperature is sought.

Thus, phospholipids having hydrophobic tails which are greater than or equal to 14 carbon atoms in chain length are preferably chosen, said chain optionally having unsaturations, such that said layer II is in the fluid state at the temperature for use.

It is advantageous to note, for example, that C14 elements are generally fluid at a temperature of greater than 23° C., whereas C16 elements are fluid only from 37° C., and C18 elements above 50-55° C. However, the use of C18 tails which have unsaturations makes it possible to decrease the phase transition (crystalline state-fluid state) temperature.

Nevertheless, for some applications or methods of detection, it may be preferred for the layer II not to be fluid at ambient temperature, but only at higher temperatures. In particular, this method will be preferred if it is desired to "memorize" the organizational state of the floaters, using a decrease in temperature to fix the structure after an organization phase at higher temperature. This will in particular be the case if there is a risk of the detection technique (near-field microscopy for example) or the conditions for analysis (dehydration for example) altering the structure.

The nonmodified phospholipids of the layer II have no particular characteristics besides the mobility properties already described; however, it is preferable for them to have polar heads, chosen from the group consisting of neutral polar heads carrying no charges, polar heads which are neutral overall but which carry opposite charges (zwitterionic polar heads), or polar heads carrying an overall negative charge.

The choice of the charge carried by the phospholipids may prove to be advantageous, in particular for reducing the phenomena of nonspecific absorption of the test nucleic acids on the layer, which are decreased when the charge of the phospholipid heads is negative. The use of neutral heads (either uncharged or carrying several opposite charges) is also envisioned.

The layer II is assembled on the layer I conventionally, via the interactions which exist between two hydrophobic elements in an aqueous medium. Reference may therefore be made to a self-assemblage layer.

However, in certain cases, a suitable catalyst, called fusogenic agent, will be used to facilitate this fusion. Thus, such agents, such as $Ca^{++}$ cations, the ethylene glycol polymer (PEG) or detergents, will be used according to protocols known to those skilled in the art.

As regards the layer I, it comprises hydrophobic elements with a chain length of approximately 2 to 2.5 nm, for example of between 12 and 20 carbon atoms, preferably between 14 and 18 carbon atoms.

It is in fact advisable to have a layer I which is particularly homogeneous. Moreover, the chain length for the elements of the layer I is preferably sufficiently long so that the coming together of the two layers I and II forms a true bilayer. The elements of the layer I are linear or branched and optionally carry unsaturations. It is important for this layer I to be homogeneous, since it serves as a support for depositing the layer II.

The layer I is attached to the support of the cell according to the invention covalently, or via strong noncovalent bonds. This method of bonding to the support is not of great importance for the implementation of the invention. Thus, in a particular embodiment, said layer I comprises phospholipids linked to said support via their polar heads. In another embodiment, said layer I comprises hydrophobic elements linked to said support via a covalent bond, for example an alkyl-thiol bond or an alkyl-siloxane bond, depending on the nature of the support.

It may be advantageous to have a support-layer I bond which is covalent, for facilitated re-use of the cell according to the invention. In fact, when the nucleic acid is linked to the protein and the protein is linked to the layer II by reversible bonds, the cell can be readily regenerated by the action of elements (or conditions) which make it possible to break the nucleic acid-protein and protein-layer II bonds and to eliminate the layer II by the action of an appropriate detergent. It is thus readily seen that a nonreversible covalent bond between the layer I and the support makes it possible to reconstruct a cell. It is obvious that if the layer I is linked to the support via a reversible bond, it is possible to recommence preparing the cell, but with an additional step.

The re-use of the support can prove to be very advantageous insofar as said support must be virtually flat at the atomic level and, moreover, can include all or part of the system for detecting the state of the cells, which can pose certain manufacturing restrictions and increase the production costs for the cell according to the invention.

Thus, in a preferred embodiment, the flatness of said support is such that the difference in height between two zones less than 100 nm apart is less than or equal to 10 nm, preferably less than or equal to 3 nm, more preferably less than or equal to 2 nm.

Various materials may be chosen for producing the base of the cell according to the invention, in particular a material chosen from the group consisting of glass covered with a layer of gold, of cleaved mica, of silicon or of any other monocrystalline material.

Monocrystalline silicon is a very advantageous material insofar as it is effectively flat on an atomic scale, and it can readily be subjected to microetching and varied chemical modifications, which makes it possible to produce a support having a plurality of cells according to the invention. Moreover, silicon has conducting or optical properties which may prove to be very advantageous as regards the detection of biological events taking place on the cell according to the invention.

As will be developed, the cell according to the invention may comprise several identical or different proteins linked to identical or different nucleic acids.

When different primers are used, a target nucleic acid complementary to two primers will be capable of binding the corresponding two floaters, which will accentuate its interaction with the support and will prime a change in spatial organization of the floaters within the cell.

Thus, when the nucleic acid IV-protein III and protein III-layer II bonds are reversible, it is possible, via agents which compete with the floater-support interaction (histidine, imidazole, EDTA), to readily differentiate the degrees of hybridization.

Moreover, the aspect of two-dimensional reorganization of the floater and primer nano-objects on the flat membrane surface, obtained through the fluidity of the layer II, falls within the area of the self-organization of biological molecules and of the physicochemical phenomena which ensue from these collective movements.

Thus, using a random distribution of the protein-nucleic acid blocks, it is clear that the action of an effector (for example a target molecule) will engender a radical restructuring in two dimensions.

When use is in particular made of a cell in which two (or more) different primers are present, the presence in the target sample of a nucleic acid which can hybridize to these various primers and which allows said blocks to become bridged should lead to a process of elongation (one-dimensional organization) at the surface of the cell.

There is therefore a change, and this is one of the major advantages of the invention, from a more or less disorganized system (random, or with an unstable equilibrium) to a highly ordered system, under the effect of the presence of the target nucleic acid in the sample tested.

Moreover, this organization is extremely sensitive to the geometric conformation of the nucleic acid and therefore to any factor (mismatching, protein binding, chemical agent) capable of interacting with the conformation or the structure of the nucleic acid.

Similarly, when the binding of any protein or of any ligand to a (single-stranded or double-stranded) nucleic acid linked to the protein anchored in the layer II is studied, or when the binding of an effector molecule on a protein (of the transcription factor type) linked to a nucleic acid, on a cell according to the invention, is studied, a modification of the structure (for example curvature of the nucleic acid) and of the equilibrium of the system are then observed (due to the introduction of these elements), which modifications can then be readily observed by various methods capable of detecting the organizational change in the cell, and in particular via an optical (absorbance, fluorescence), electrical, electron-based, surface plasmon resonance, energy transfer, radio-labeling, diffraction (optical, electrical, X-ray, neutron diffraction) or microscopy (direct optical or fluorescence microscopy, electron microscopy, near-field microscopy, atomic force microscopy) system.

This disorder-order phase change observed when an event occurs on an atomic scale can only be readily detected when the protein on the cell according to the invention has what has been called "an unequivocally detectable geometry" and when the nucleic acid is attached thereto unequivocally.

The principle of the invention is therefore the mobility of the protein anchored in the layer II, allowing a reorganization of the system, and the fact that the protein-nucleic acid unit is unequivocal and non-random, which makes it possible to detect said reorganization.

It is also envisioned that the presence of a single target nucleic acid molecule in the sample tested will make it possible to induce a reorganization which may then be detected.

An example of the implementation of such a method would be to pre-organize the cell with a nucleic acid of the same nature as that to be detected, but which, firstly, has a lower affinity for the primer than the nucleic acid to be tested (modified base, mismatch) and, secondly, has a geometry (size, curvature) which is different from the nucleic acid to be tested. The exchange of a single nucleic acid (external competitor molecule) within a pre-organized cell will then lead to a local structural defect.

It is known by those skilled in the art that a single defect within a "crystalline" network destabilizes the entire network. If the cell size is chosen in an appropriate manner, it is reasonable to hope that this single event will change the stability of the organization of the cell. Such a change in stability can be tested by gradually applying an outside (chemical, temperature, electric potential, etc.) factor which destabilizes the cell as far as disorganization. This principle opens up the possibility of detecting single molecular events and corresponds to the theoretical maximum sensitivity of a detector.

This sensitivity is an enormous advantage compared to the other existing widely used systems, which require the presence of a large number of nucleic acid molecules in the sample in order to be detected.

Moreover, such a detector associated with a receptor protein chosen in an appropriate manner in order to see its interaction with the modulated DNA can be the basis of a molecular detector for an infinite variety of molecules of interest (in particular proteins, medicinal products, pollutants).

It is also important to note that the hybridization as such is not detected, but rather the changes induced in the cell according to the invention. Thus, this implies that the cell according to the invention (or the support displaying a plurality of cells) can be used for detecting a target in a sample without it being necessary to label or to excessively handle said sample. This is also a considerable advantage, since it is thus possible to detect the presence of mRNA without having to first convert it into cDNA.

It should be noted that the geometric conformation of ssDNAs and dsDNAs is so different that it results in very distinct physicochemical properties. Thus, after hybridization, it is in particular possible to detect this effect by a change in the electronic conductivity of the cell according to the invention. This is particularly easy when the protein according to the invention also has a redox center.

It is also possible to detect the hybridization by surface plasmon resonance, or by an optical method, which is facilitated by the presence of a protein exhibiting an anisotropic optical absorption.

In order to carry out the simultaneous detection of several targets, the invention therefore also relates to a support displaying a plurality of cells according to the invention.

The various cells may be separated from one another by microetching on the support, or by the presence, between two cells, of a hydrophobic layer consisting of elements with a chain length different from (preferably less than) the chain length for the elements of the layer I, for example less than or equal to 5 carbon atoms ("differential patterning" Cheng et al., 2000). These elements having a low-carbon-number chain can be deposited onto the support using the masking techniques common in microelectronics.

The support according to the invention is advantageously completed by the setting up of a system for measuring the current, the impedance or the potential, making it possible to detect the events occurring on each one of the cells.

Another preferred alternative is that the support comprises a surface alternating conducting and reflecting zones and nonconducting and transparent zones. Such a network comprising transparent zones clearly smaller in size than the wavelength of visible light has been described as having a function of light transmission according to wavelength in the form of a "comb" (Ebbesen et al., 1998). The optical transmission properties of such a structure should be altered by the state of the neighboring cells, which provides a possible reading means.

It can also be envisioned that the support according to the invention comprises, between each cell, an integrated optical device (laser-photodiode couple for example) capable of measuring the absorbance of a cell in two cross directions and of deducing therefrom its state of organization (anisotropy) or of disorganization (isotropy).

It is also possible to preferably envision reading the organizational state of each cell via a laser optical scanning device sensitive to the change in light polarization. Such a device capable of reading cells which are submicron in size is commonly used by the general public in minidisc readers and rewritable CD-Rom readers. In such a case, the variation in polarization of the reflected light normally provided in magneto-optical discs by a reorganization of the crystalline network of a rare earth salt (europium, and other compounds of the same transition series of the Mendeleiev table) by a magnetic field and laser heating, would, in the system described in the invention, be provided by the variation in spatial organization, in the cell, of the protein or of its cofactor, which are objects which are optically active in terms of polarization, ellipticity (differential absorption of polarized light) and optical absorption.

The invention also relates to a method for identifying the presence of a test nucleic acid in a sample, comprising the steps of:

a) bringing said sample into contact with a cell according to the invention, under conditions which allow the hybridization of said test nucleic acid to a nucleic acid attached to a protein of said cell, b) detecting the hybridization of said test nucleic acid to said nucleic acid attached to said protein.

The detection can be carried out by any means mentioned above. If the test sample has been labeled, the detection can be carried out as a function of said labeling. However, it may be preferred to detect the presence of the target nucleic acid by a change in conformation of the system. Thus, the cell according to the invention allows the detection without there having been any need to label the test sample.

The invention also relates to a method for identifying the binding of a protein to a nucleic acid, and/or its activity on the conformation of said nucleic acid, comprising the steps of:

a) bringing said protein into contact with a nucleic acid attached to a protein, in a cell according to the invention, b) detecting the binding of said protein to said nucleic acid, and/or its activity on the conformation of said nucleic acid.

Said nucleic acid may be single-stranded, double-stranded or triplex, when a nucleic acid has already been attached to one of the nucleic acids (primers) of the cell. It is clear that the choice of certain bases for the primer can lead to the formation of a triplex nucleic acid, said formation then being considered, for the purpose of the invention, as a hybridization.

The detection can also be carried out in several ways, and in particular by a change in conformation of the system.

The invention also relates to a method for identifying the binding of a ligand to a protein attached to a nucleic acid attached to a protein in a cell according to the invention, comprising the steps of:

a) bringing said ligand into contact with said protein, b) detecting the binding of said ligand to said protein.

Among the ligands and proteins envisioned, studies are in particular carried out in order to identify effector molecules which bind to nuclear receptors or transcription factors. The binding may be direct or indirect, and may involve, for example, the binding of the ligand to a receptor which will then attach to a protein or a protein complex already associated with the DNA of the cell.

The binding of the ligand to the protein can be observed in particular by a change in conformation of the system.

In general, the invention relates to a method for identifying the binding of a compound to a nucleic acid, and/or its activity on the conformation of said nucleic acid, comprising the steps of:

a) bringing said compound into contact with a nucleic acid attached to a protein, in a cell according to the invention, b) detecting the binding of said compound to said nucleic acid, and/or its activity on the conformation of said nucleic acid.

As above, said nucleic acid may be single-stranded, double-stranded or triplex, when a nucleic acid has already been attached to one of the nucleic acids of the cell.

The binding is in particular detected by a change in conformation of the system, as was explained above.

The detection of the geometry or of the disturbance of the geometry of the Floater-Primer-Target assemblies can advantageously be carried out through the contribution of atomic force microscopy technology in a liquid environment. Thus, the potential applications of this type of characterization relate to studying the impact of the interaction of any molecules or macromolecules with nucleic acids (regulation, transcription factors, drugs, medicinal products, in particular for chemotherapy, etc.).

In a particular case, the device according to the invention offers a molecular and supramolecular proximity involving a lipid membrane, redox proteins and nucleic acids. This assembly of electro-active and optically active biomolecules within microsystems derived from microelectronics may potentially prove to have a great impact in electron transduction (conductors, semi-conductors, biomolecular circuits) and nonlinear optical transduction (anisotropic) fields.

In fact, double-stranded DNA, unlike ssDNA, has properties of electron transfer according to a process of electronic conduction by overlap of the Pi orbitals. In addition, the hybridization reaction between two ssDNA molecules is very specific.

The current systems developed in the context of electronic components on a nanometer scale come up against various problems, including:

the interconnection of the nano-objects with one another,
the connection of the nanostructures to macroscopic electrodes.

The use of processes of molecular recognition and of self-assembly of molecules within supramolecular structures, as envisioned within the cell according to the present invention, might make it possible to circumvent these difficulties.

In fact, the cell according to the invention exhibits an original biomolecular architecture which falls within the field of nano-bioengineering, i.e. of the development of novel types of nanostructures having properties of:

strong modularity,
high degree of organization on a molecular scale,
vectorial electron transfers,
coupling with chemical messengers.

DNA has the mechanical molecular recognition properties for being integrated into microcircuits. However, the intrinsic electronic properties of this macromolecule appear to be insufficient to be used directly (Braun et al., 1998). One of the most promising areas of research in the use of electrical charge transport potential along the DNA duplex is represented by the use of electrocatalytic processes (Boon et al., 2000).

Such a signal transduction device can absolutely be integrated into the device according to the invention through the use of additional redox molecules.

However, in a preferred device according to the invention, the presence of floaters composed of redox proteins having electroactive groups and/or redox potentials which are different and which can be modulated makes it possible to provide an electron environment which is dense in terms of overlap of electron orbitals. Depending on the periodicity and on the two-dimensional organization of these redox macromolecules (then considered to be relay centers), such a structure might give rise to electron doping of DNAs, to electron jumping between proteins or to energy transfer processes.

Thus, a cell according to the invention may have methods of use other than the simple methods of detection which have been mentioned above.

The invention also relates to a method for preparing a cell according to the invention, comprising the step of:

introducing, on a support which is substantially flat on an atomic scale, a protein III having an unequivocal three-dimensional structure (stable and defined spatial organization), linked to a nucleic acid IV, such that the nucleic acid-protein assembly is laterally mobile relative to said support, in order for the hybridization of a target nucleic acid to said nucleic acid IV or the change in conformation of said nucleic acid IV to be detectable via the geometric reorganization of the nucleic acid-protein assembly.

The invention also relates to a method for preparing a cell according to the invention, comprising the steps of:

attaching a hydrophobic monolayer I to a support which is substantially flat on an atomic scale,
assembling, on said monolayer I, a mono-layer II comprising phospholipids,
introducing a protein III having an unequivocal three-dimensional structure, said protein III being laterally mobile in said layer II, via a bridging molecule having a hydrophobic end capable of interacting with the monolayer II, and an end which has been chemically functionalized so as to form a stable bond with a protein III, said protein III being attached in an-unequivocal manner to a nucleic acid IV, preferably via a molecular arm.

B: The variation in signal corresponds to the injection into the fluid circuit of a DMPC-DOGS mixed vesicular solution produced in water. The increase in the signal corresponds to fusion kinetics for the vesicles on the support so as to obtain a compact lipid monolayer. Thus, after 20-40 min of injection, a return to the working buffer makes it possible to estimate the amount of lipids assembled at 1700±300 RU. This value, according to the various modes of calibration proposed by BIAcore, corresponds to that of a lipid half-membrane.

C: A procedure for treating the membrane with a 20 mM sodium hydroxide solution makes it possible to remove the excess lipids adsorbed onto the structure.

D: Control of the homogeneity of the lipid membrane by injection of water-soluble protein (for example cytochrome c, BSA, etc.).

Figure 2:
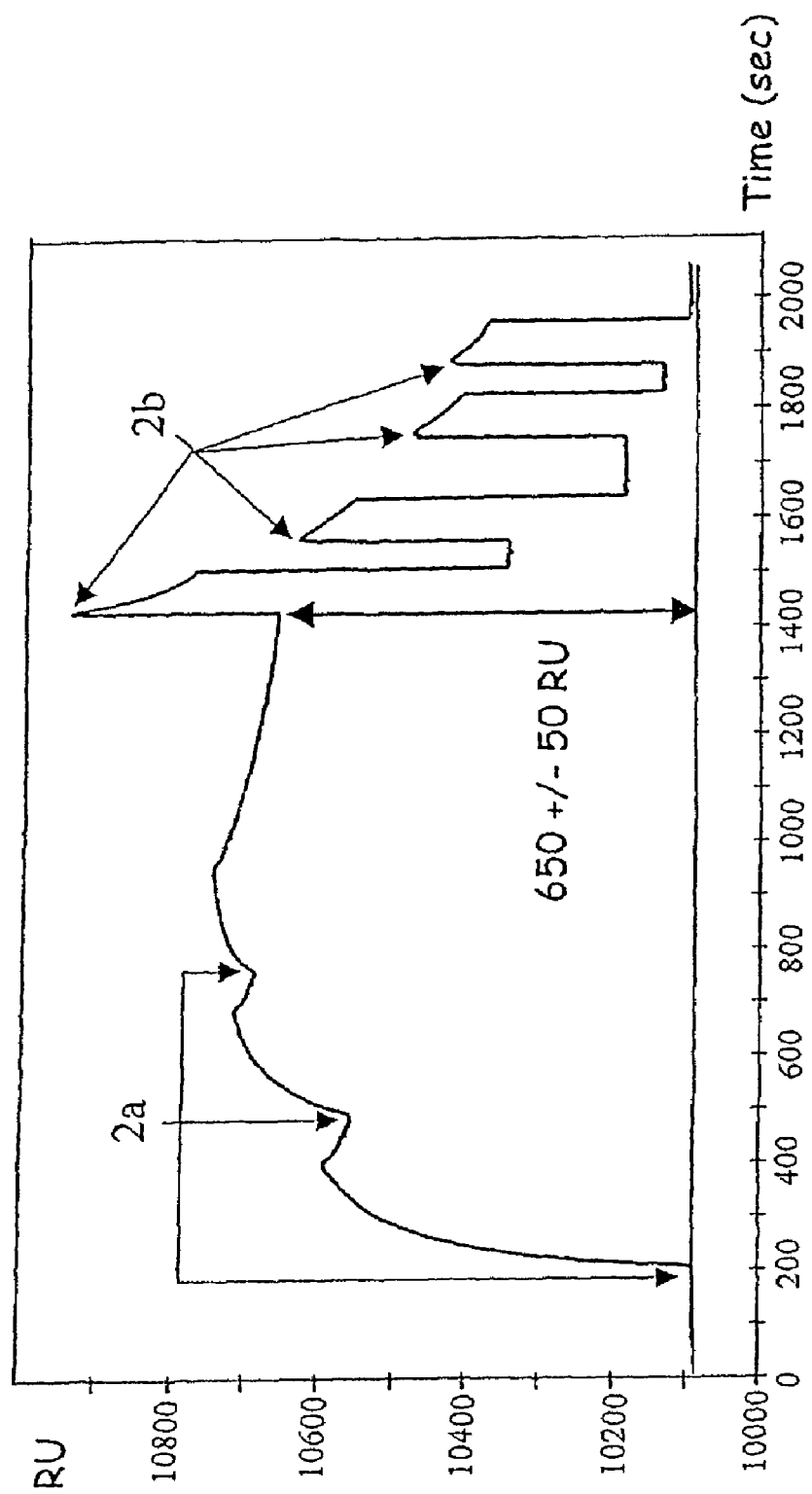

FIG. 2 Demonstration of a specific association of Hb5 (His)4 on the hybrid bilayer functionalized with chelating nickel cations Characterization by SPR A: Three successive injections (represented by arrows) of the cytochrome b5 polyhistidine form are carried out in the region of the functionalized lipid bilayer. Conventionally, the protein solution, which has a concentration of 1 µM in 50 mM phosphate buffer, pH 7, is injected at a flow rate of 10 µl/min for 180 seconds. The various injections produce a gradual saturation of the surface. The maximum covering is of the order of 650±50 RU, i.e. a degree of surface covering of 7 pmol.cm$^{-2}$.

B: In order to show the great specificity of the interaction, injections of a 1 mg/ml solution of histidine in 50 mM phosphate buffer are carried out (for example: four injections marked with arrows). The injection of an agent which competes with the chelation between the polyhistidine segment of Hb5 (His)4 and the membrane. Each injection (flow rate 10 µl/min for 120 seconds) is accompanied by a decrease in signal, i.e. in the amount of proteins interacting with the membrane. Thus, complete regeneration of the structure is obtained after a contact time of a few minutes.

Figure 3:
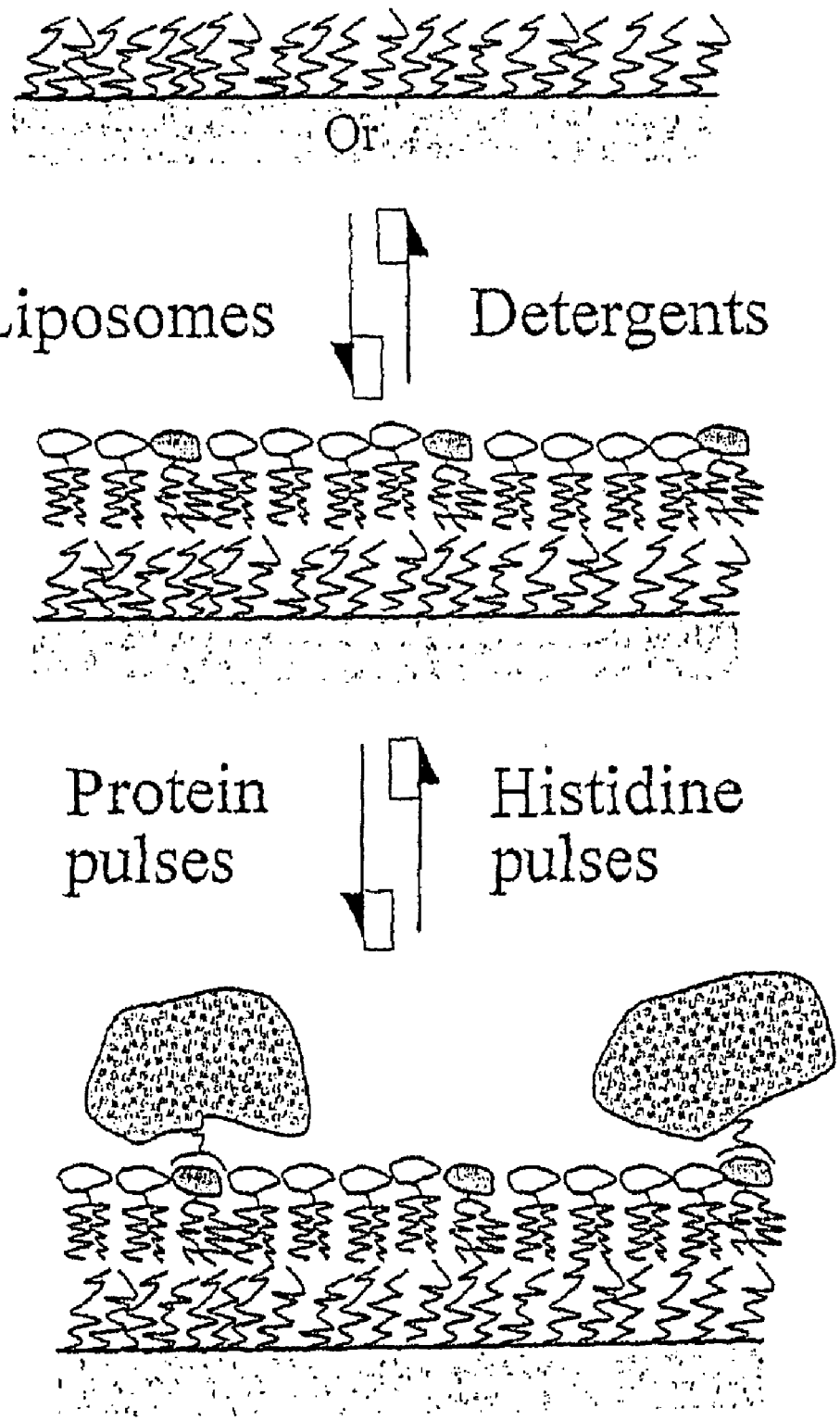

FIG. 3 Diagram of the membrane biosensor, construction/regeneration of the supramolecular assembly Construction:

An inorganic surface (for example: gold) is functionalized with a dense monolayer of octadecyl mercaptan. This surface is suitable for the fusion of lipid vesicles (liposomes) until a dense monolayer of phospholipids is obtained above the support. The presence of 10% (mol/mol) of modified phospholipids allows the anchoring of cytochromes b5 so as to obtain a dense monolayer of proteins.

Regeneration:

Injections of agents which compete with the affinity via metal ions, such as a solution of histidine (1 mg/ml), make it possible to detach all the Hb5(His)4 interacting specifically with the support. Similarly, the lipid half-membrane reconstituted on the functionalized inorganic support can be regenerated using a solution of detergent such as octyl glucoside, or OG (40 mM in $H_2O$).

Thus, all of the constructing and destructuring phases can be carried out in a controlled manner using an aqueous solution which preserves the integrity of the biological molecules.

Figure 4:
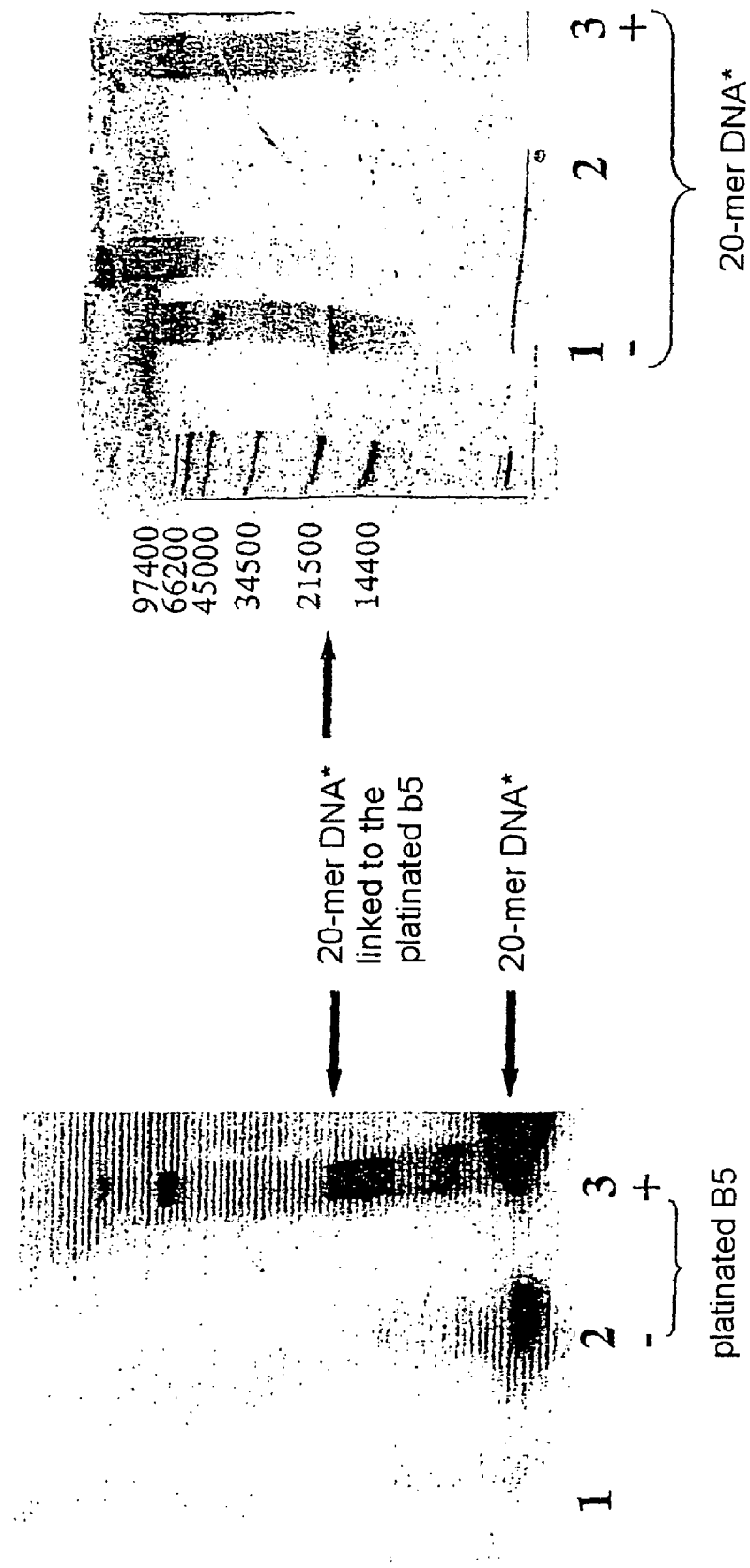

FIG. 4 Characterization of the b5-cis-Pt-ssDNA complex, SDS-polyacrylamide (15%) gel of Hb5(His)4 platinated and coupled with an oligonucleotide of sequence CTAT-CATTTGCTTACTATTC (SEQ ID No. 13)

FIG. 4.A Autoradiogram of a gel into which Hb5(His)4-cis-Pt has been injected; the $^{32}$P-radiolabeled oligonucleotide (well 2) and the b5-cis-Pt-ssDNA complex (well 3) make it possible to demonstrate the appearance of an additional radioactivity signal in well 3 compared to well 2.

FIG. 4.B Use of a polyacrylamide gel (15%) under denaturing conditions (SDS). Cross-characterization of the b5-cis-Pt-ssDNA complex: said complex injected into lane 3 exhibits a band which makes it possible to confirm the existence of a population whose molecular weight is close to 20000 Daltons, i.e. the theoretical molecular weight.

Well (1): b5 platinated with cis-Pt[$(NH_3)_2(H_2O)_2$]$^{2+}$.

Well (2): radiolabeled 20-mer DNA (DNA*). Well (3): platinated b5 linked to the 20-mer DNA*

Figure 5:
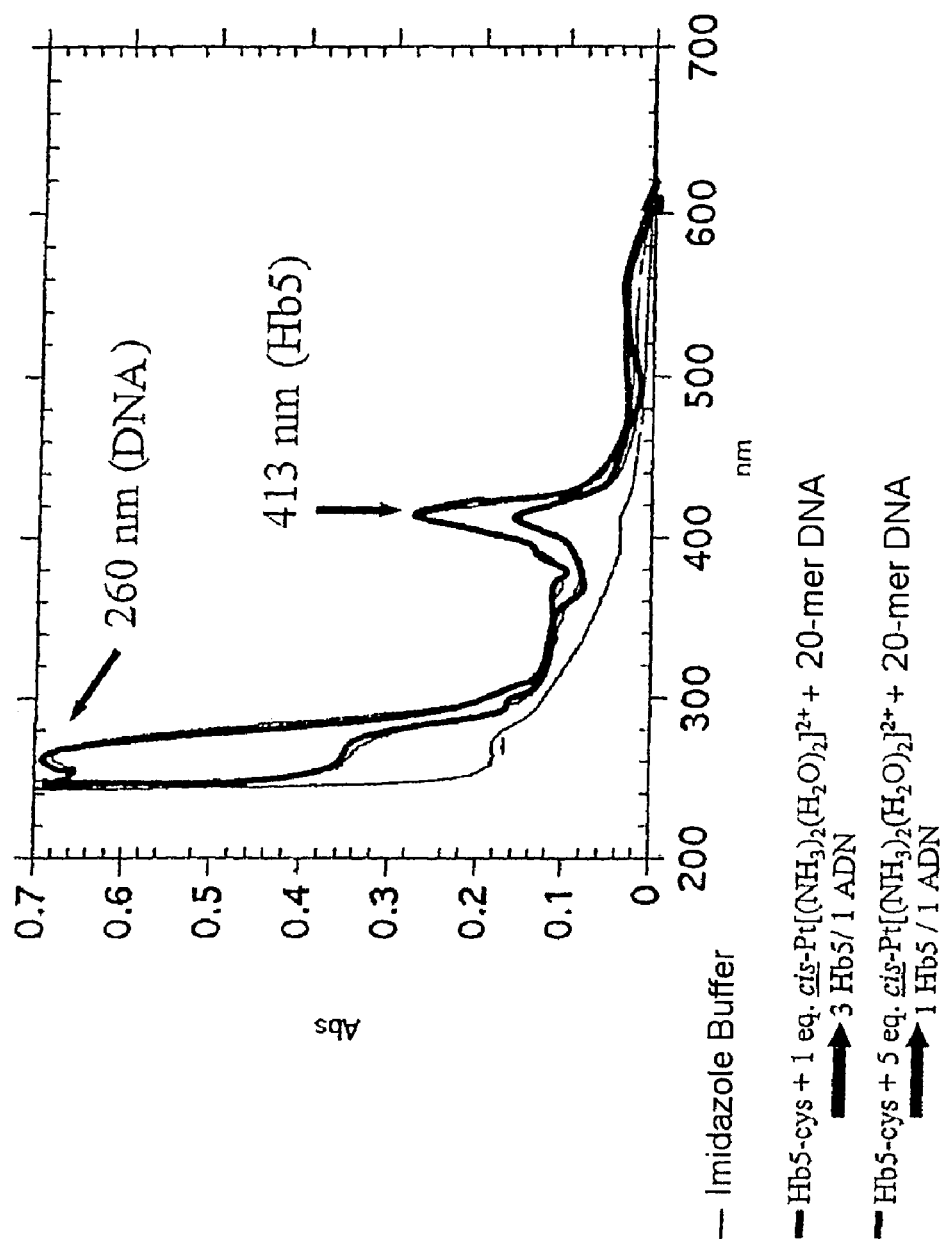

FIG. 5 Spectral characterization of the complex Hb5(His)4-CTATCATTTGCTTACTATTC via cis-Pt[$(NH_3)_2(H_2O)_2$]$^{2+}$bridging Two procedures for reconstituting the Hb5 (his)4-cis-Pt-ssDNA complex are characterized by spectrophotometry in a 240-600 nm window. The cytochrome b5 has an absorption maximum at 412 nm whereas the ssDNA has a maximum at 260 nm. The spectral profile of two samples and also the relative quantification of each species by virtue of the molar extinction coefficients make it possible to demonstrate:

red spectrum: an Hb5(His)4/ssDNA molar fraction=3/1 blue spectrum: an Hb5(His)4/ssDNA molar fraction=1/1

The procedure for the characterization represented by the blue absorption spectrum makes it possible to obtain equimolar coupling.

Figure 6:
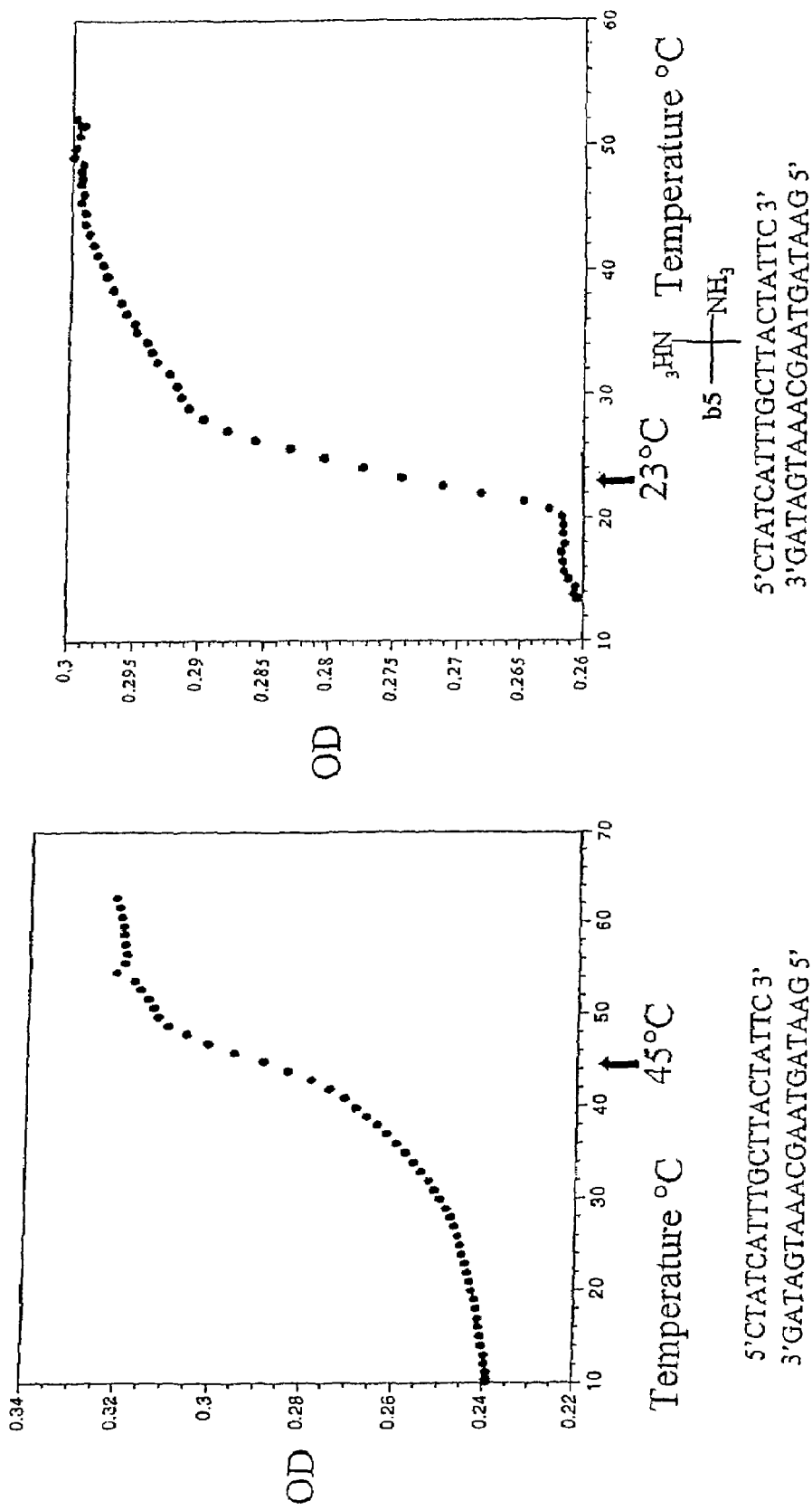

FIG. 6 Determination of the melting temperatures of the 20-mer DNA and of the 20-mer DNA bridged with platinated Hb5(His)4

The melting temperatures were determined by spectral measurements of hyperchromicity after melting of the complementary strand at high temperature (80° C.). A decrease by steps of 1° C. makes it possible to follow the evolution of the dsDNA spectrally.

The results of absorption as a function of temperature for the free ssDNA makes it possible to obtain a curve whose inflexion point corresponds to the melting temperature. The Tm for the ssDNA is evaluated at 45° C.

The same characterization on the ssDNA coupled to Hb5(His)4 gives a modified profile, the Tm of which was estimated at 23° C.

Figure 7:
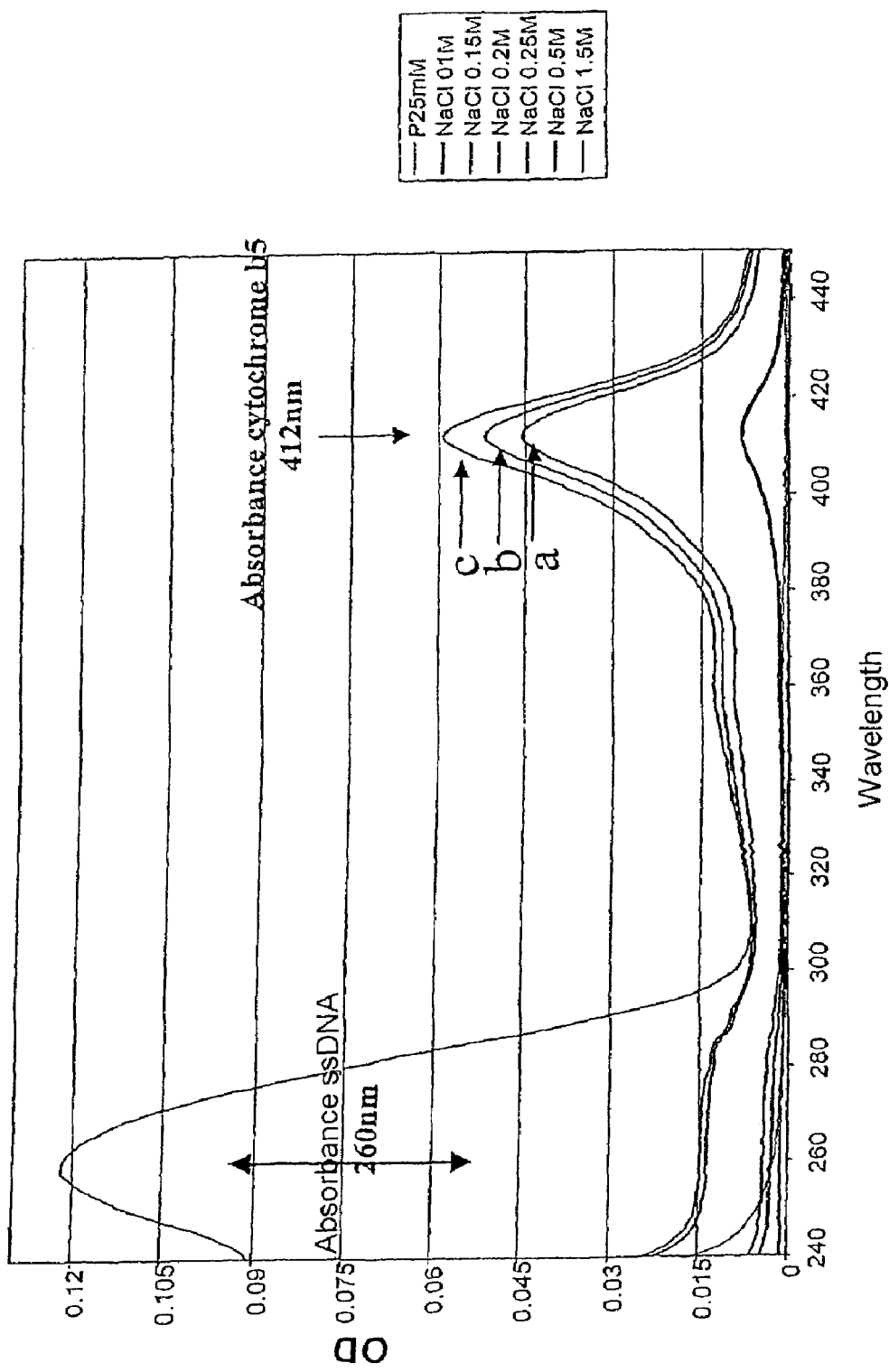

FIG. 7 Separation of the protein species and of the cytochrome b5-ssDNA complex via a DPDPB bridge, by chromatography. Characterization by spectrophotometry at 240-450 nm The various populations derived from the incubation (4 H at 30° C.) of ssDNA-DPDPB with Hb5(His)4mut24 are loaded onto a DEAE column. The various species are then eluted via a 25 mM phosphate solution and an increasing NaCl gradient.

The cytochrome b5 has an absorption maximum at 412 nm whereas the ssDNA has a maximum at 260 nm.

The NaCl gradient makes it possible to gradually elute all the populations:

[NaCl]<0.15M: population 1 of Hb5(His)4mut24

0.15<[NaCl]<0.25 M: population 2 of Hb5(His)4mut24

[NaCl]=0.5 M: population 3 of Hb5(His)4mut24

Figure 8:
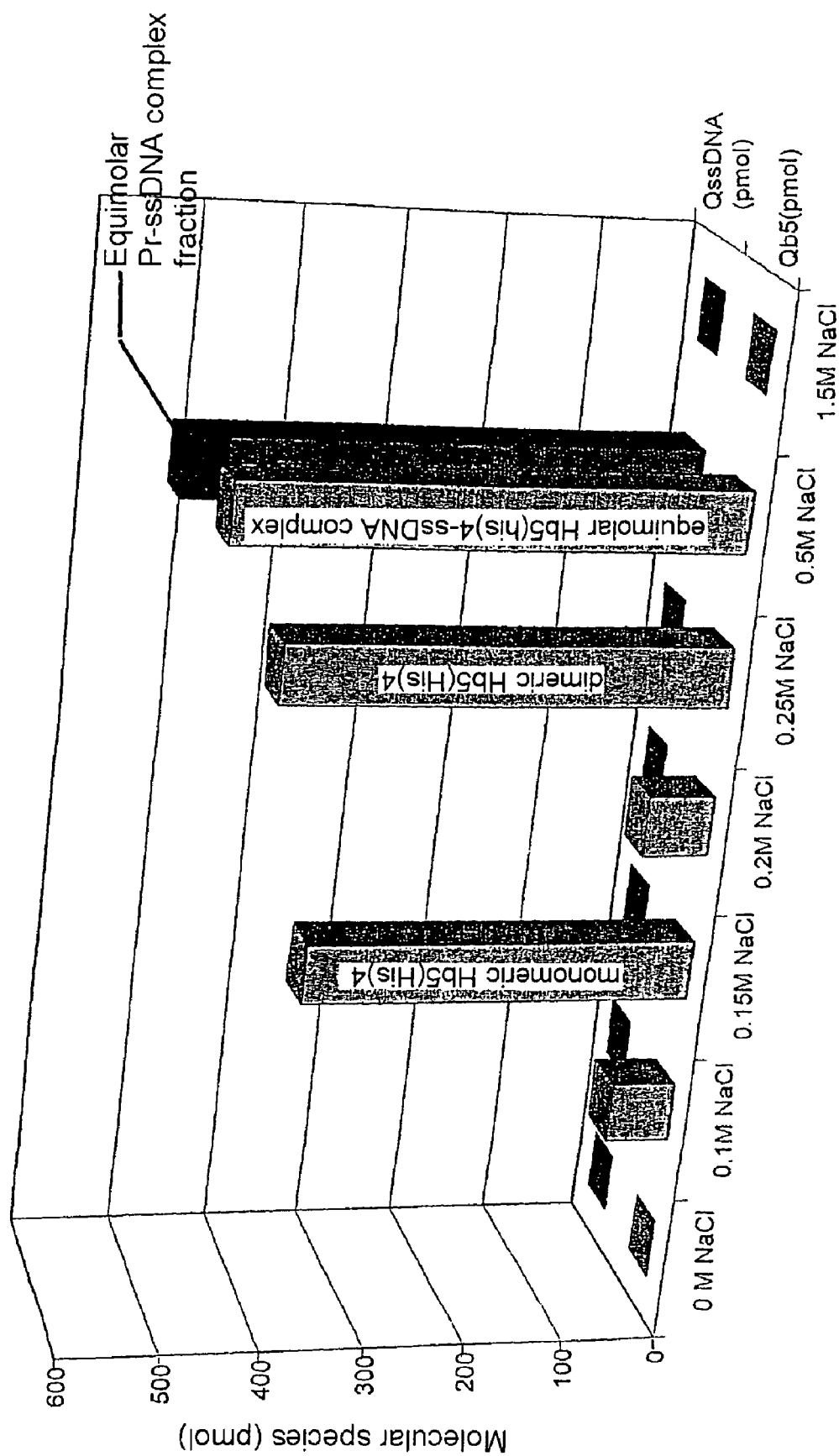

FIG. 8 Elution profile and supramolecular composition of the cytochrome b5-ssDNA complexes The molar quantification of the species isolated after separation on DEAE is represented in the form of a histogram:

Populations 1 and 2 of Hb5(His)4mut24, characterized in FIG. 7, show no ssDNA component measured at 260 nm. These two populations correspond to the monomeric form (which is not reacted during the incubation) and to the dimeric form (resulting from a cystine bridge between two proteins).

Population 3 shows an equimolar Hb5(his)4mut24-ssDNA complex.

Figure 9:
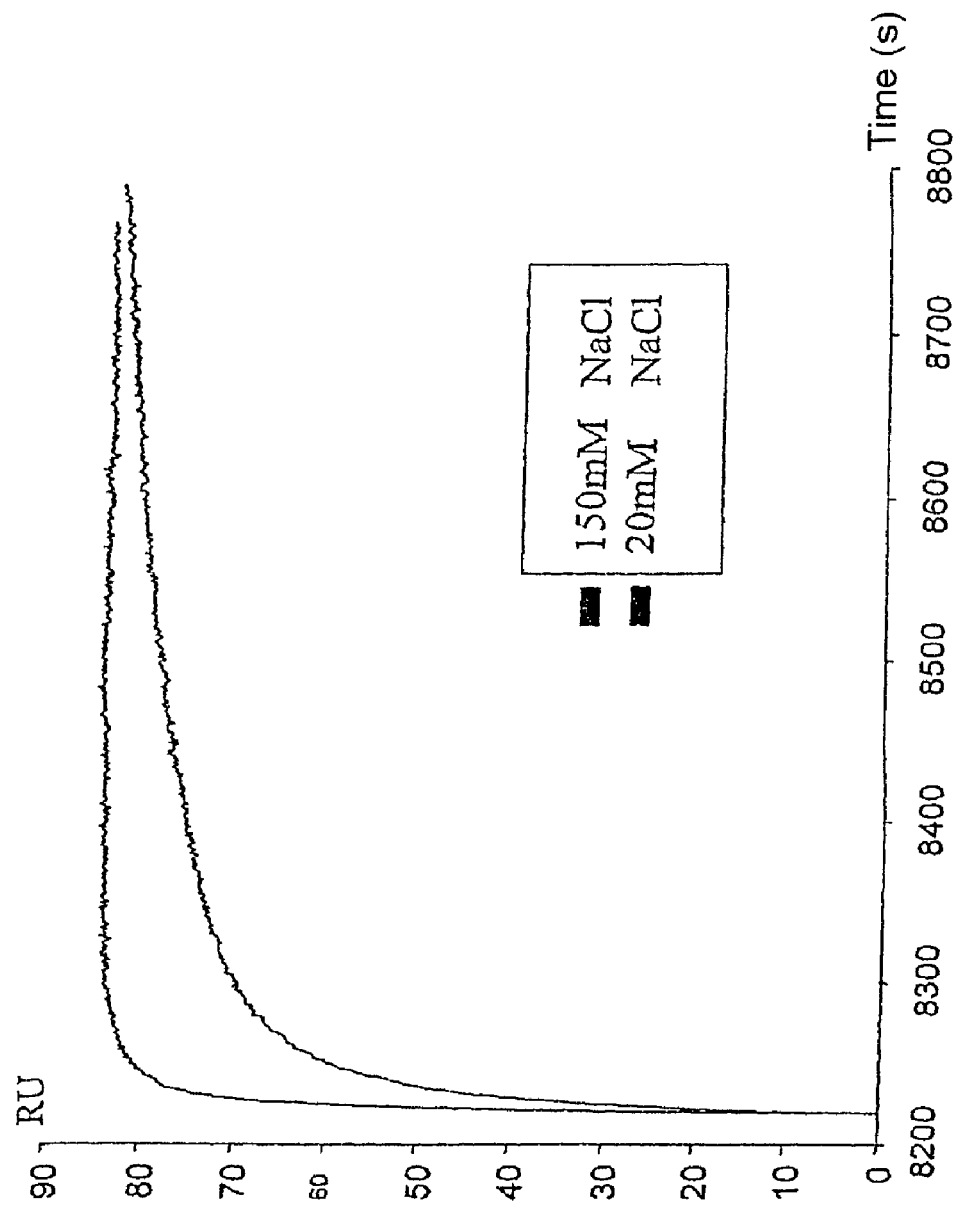

FIG. 9 Detection by surface plasmon resonance of the kinetics of association of an ssDNA complementary to the primer ssDNA interacting with the biosensor Starting from a "b5-W1" signal in the region of 250 RU, various injections of ssDNA were carried out, at a b5-ssDNA density equal to 1 pmol.cm$^{-2}$:

Thus, the ssDNA strand complementary to W1 was injected in the region of the biosensor (1 µl/min for 10 min) for two concentrations of NaCl.

At a 150 mM concentration of NaCl, a hybridization signal is observed within a complexation range corresponding to 100% of the "b5-ssDNA" assemblies interacting with the membrane.

The same oligonucleotide injected at a low concentration of NaCl (25 mM) shows very restricted hybridization with respect to the biosensor.

Figure 10:
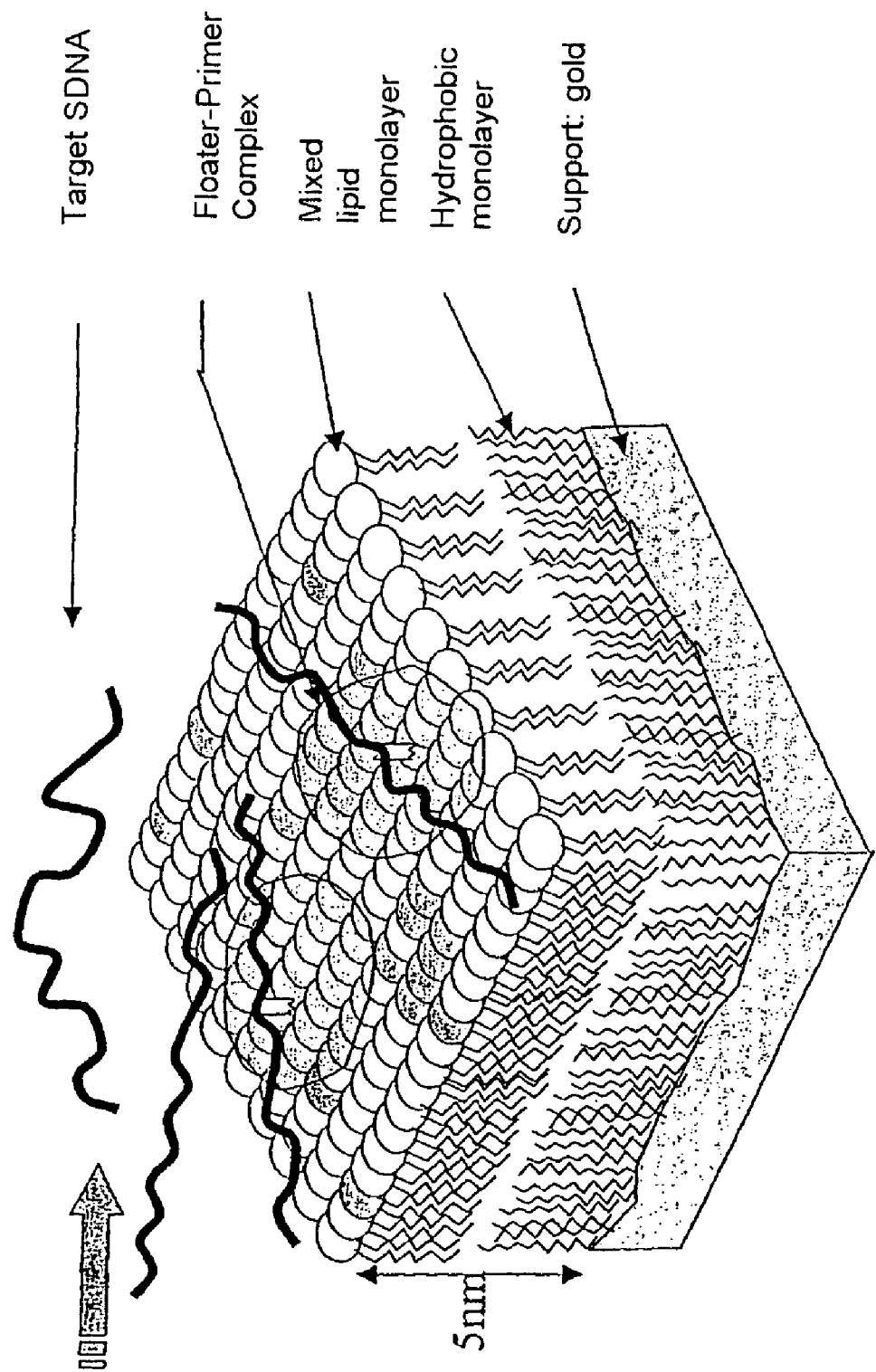

FIG. 10 Diagram of the assembly as a ~DNA biosensor

The arrow represents the flow of biomolecules of the test sample.

Figure 11:
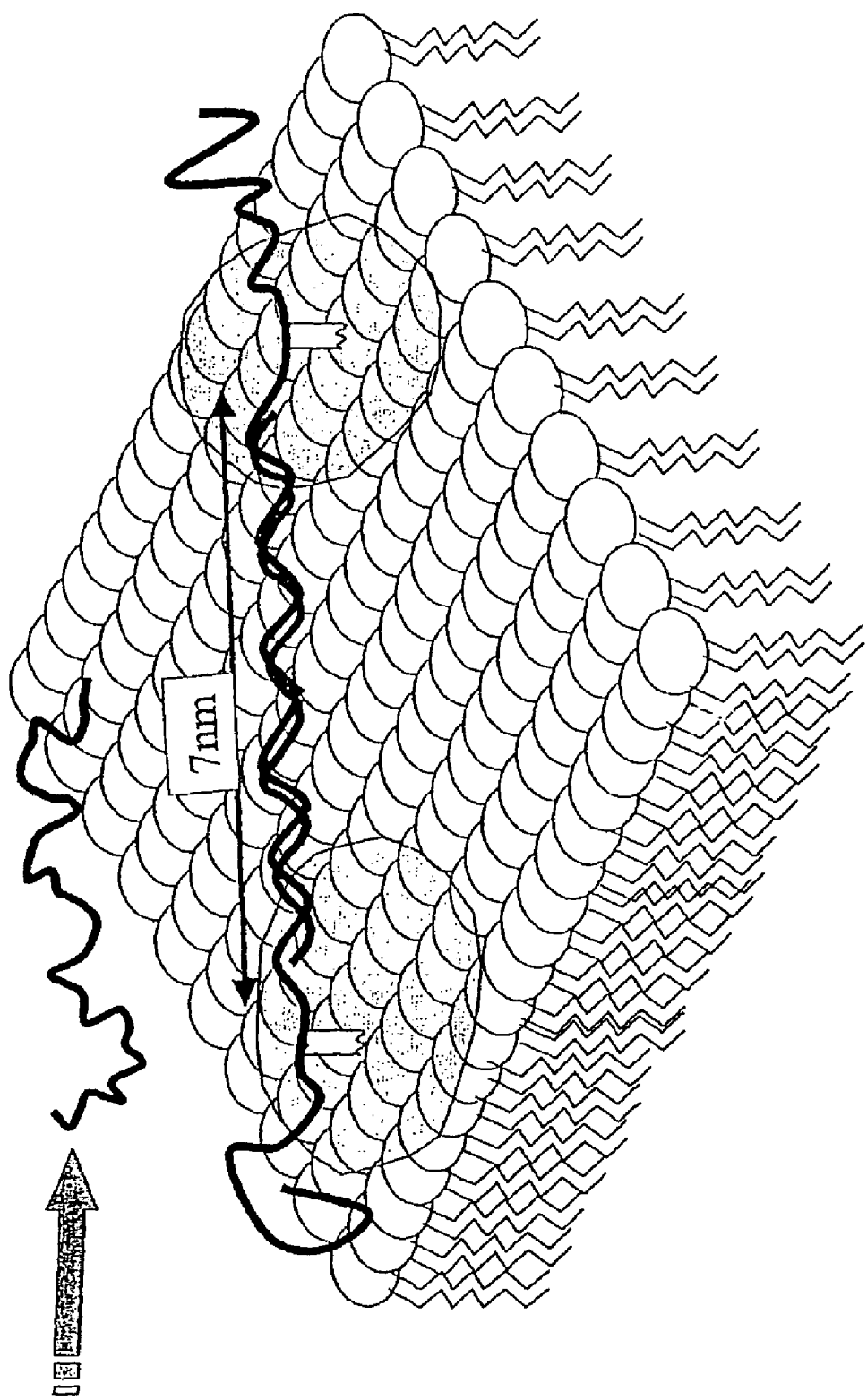

FIG. 11 Diagram of the assembly as nanostructures with dynamic and conformational properties A set of various floating blocks can be displayed at the surface of the biosensor, and the injection of an oligonucleotide which potentially hybridizes on a part of the floating blocks should allow inter-block bridging. The lateral mobility characteristic of the elements should promote this process until phenomena of supramolecular reorganization at the surface of the cell are obtained.

The following examples relate to a particular case of the invention, but should not be considered as limiting the invention.

EXAMPLES

Example 1

Preparation of the Hybrid Bilayer 1.1) Functionalization of the Support

The solid support used consists of a glass slide covered with a film of gold marketed by the company BIAcore® under the name chip J1.

Such supports were also produced by the inventors. They consist of the use of polished glass cover slips (thickness 0.4 mm, 22*10 mm, Prolabo) which are successively subjected to spraying of 2.6 nm chromium and then spraying of 48 nm of gold under a vacuum of $2\times10^6$ mmHg.

The metal interface is then covered by self-assembly of molecules of octadecyl mercaptan, or OM, from Aldrich. The OM solution is used at 1 mM in a 4/1 (v/v) ethanol/water mixture. After incubation for two hours, the slides are washed with chloroform, with methanol and then with water and are dried under a stream of nitrogen.

The result is the reconstitution on the gold of a highly organized dense monolayer which confers on the support very strong hydrophobic properties. This first assembly has been characterized many times in the literature. Contact angle measurements make it possible to routinely verify the compactness of the monolayer thus reconstituted.

1.2) Production of the Lipid Xesicles 1.2.1) Sonication/Extrusion Method

The method used to prepare the liposomes is based on a sonication/extrusion double procedure.

The dimyristoyl and/or dipalmitoyl phosphatidyl-choline phospholipids from Sigma, which are the main constituents of the vesicles, are solubilized in an organic solution of chloroform. A lipid film is then deposited in glass scintillation tubes by evaporation of the chloroform under a stream of nitrogen. This film is resuspended in an aqueous solution (of ultrapure or buffered water) at a final concentration of 1 mM.

This mixture is then sonicated:

in an ultrasound bath (Transsonic 310 from Fisher-Scientific) at maximum power for 20 min, and then with an ultrasonic disintegrator (Vibra-Cell from Bioblock) using 2 min pulses, with 50% active cycle for an outlet power of 4.

The procedure is stopped when the solution has become translucent, i.e. conventionally after 6 to 10 min of cumulative sonication time.

The final production step consists of extrusion through a polycarbonate membrane (Avestin, 19 mm in diameter and 50 nm or 100 nm in pore diameter) in a Liposofast® basic device, Avestin, Inc.

1.2.2) Vortex/Extrusion Method

A second procedure is used when molecules are used which are sensitive to ultrasonic disturbances, such as the hydrocarbon chains of some phospholipids having polyunsaturations (for example: 1,2-dioleoyl-sn-glycero-3-[(N-(5-amino-1-carboxypentyl)iminodiacetic acid)succinyl] or DOGS, from Aventi Polar Lipids, and dioleoyl phosphatidylcholine, or DOPC, from Sigma). In this case, a procedure identical to 1.2.1, consisting of solubilization in $CHCl_3$ and then construction of a lipid film on glass, is applied. The procedure then differs in that the phospholipids are resuspended in an aqueous solution at 1 mM via a step consisting of vortexing for 5 min at maximum rate.

This step is followed by a phase of extrusion through a polycarbonate membrane with a 50 nm pore diameter, in a Liposofast® device from AVESTIN.

1.3) Reconstitution of the Lipid Monolayer

The hydrophobic support serving as matrix to generate the lipid monolayer is subjected to a treatment procedure as follows: in order to improve the wettability of the structure, an ethanol/water (1/1 vol) solution is injected onto the support and is followed by steps of rinsing with water and with buffered solutions. In order to clean the interface, a solution of detergent, octyl glucopyranoside from Sigma, at a concentration of 40 mM, is injected. Immediately following this, the lipid vesicles prepared are injected in contact with the functionalized metal surface. The vesicles fuse spontaneously on contact with the hydrophobic monolayer of OM, according to a liposome fusion process established by Kalb et al. (1992). After 30 to 60 min, this process leads to the formation of a lipid monolayer completely covering the OM monolayer.

The molecular assembly thus obtained has a substrate which is metallic in nature, covalently covered with a first alkylated sheet on which is assembled a fluid and dynamic sheet of amphiphilic molecules.

The characterization experiments use the BIAcore® technology via BIAcore 1000 and BIAcore X devices.

Figure 1:
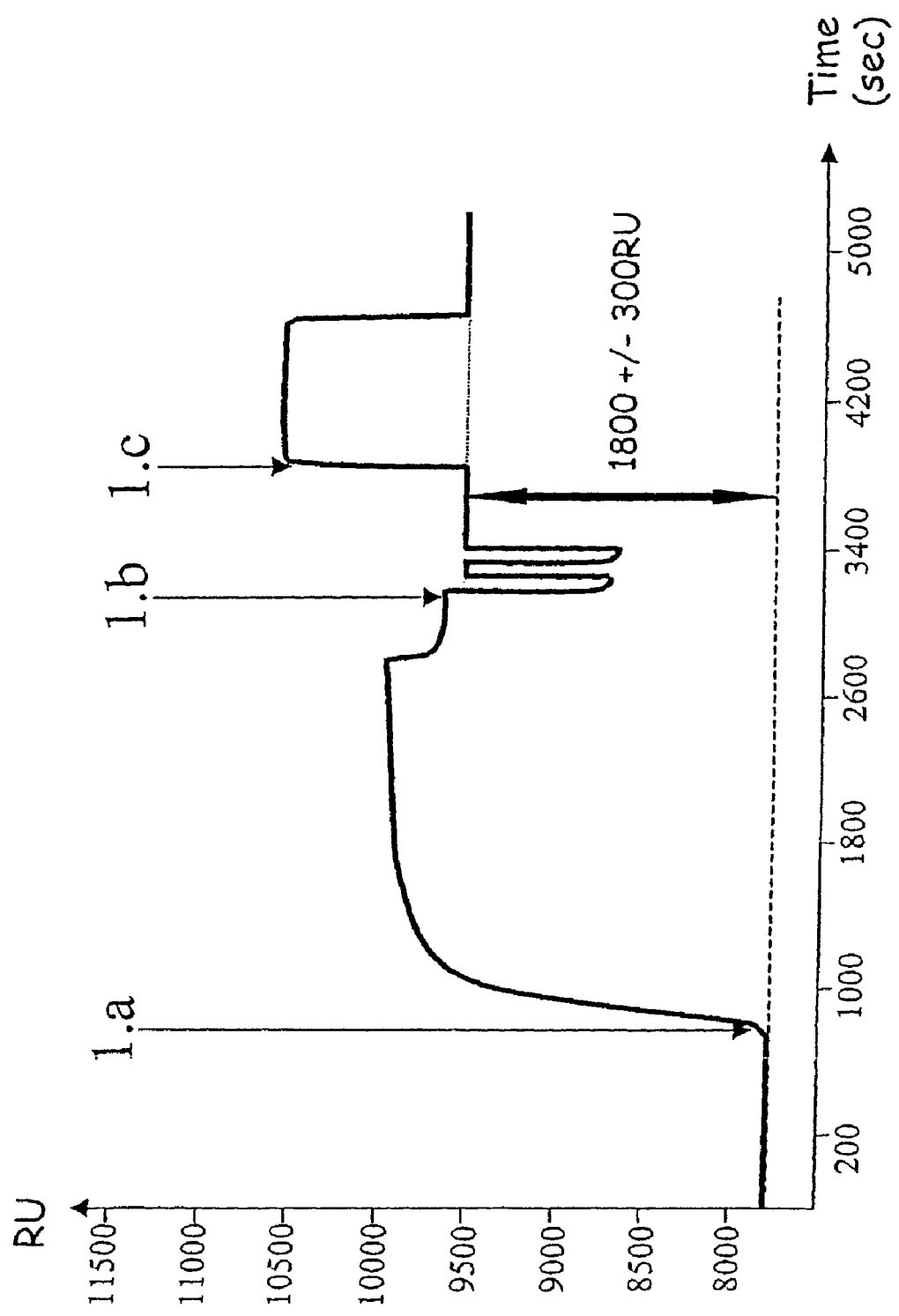
FIG. 1 Construction of the hybrid bilayer and characterization by surface plasmon resonance analysis A: The signal recorded corresponds to the base line for the metal support covered with a dense monolayer of OM in the environment of the working buffer (conventional phosphate buffer, 50 mM, pH 7.5).

The liposome fusion results are obtained in the form of a sensorgram (FIG. 1). On injection of the vesicles, a phase of association with the support is observed, producing a plateau after a contact time of 20-30 [lacuna]. On stopping the injection, and therefore on returning to the working buffer, a first amount of lipid material is evaluated. A procedure consisting of cleaning the surface with 20 mM sodium hydroxide makes it possible to remove all the vesicles incompletely fused at the surface of the biosensor. Conventionally, the signal obtained is between 1400 and 2000 RU, which is in accordance with the results available in the literature and the methods of calibration provided by the manufacturer. An injection of soluble proteins in the region of this supported membrane makes it possible to validate the absence of a defect in the upper lipid monolayer. Introduction into the liposomes of synthetic DOGS phospholipids in a proportion of 10% mol/mol confers on this monolayer protein-HisTag sensor complexation properties.

Example 2

Construction, Expression and Purification of the Fusion Proteins 2.1) The Water-Soluble Proteins with a Histidine Tag The initial protein used in the context of this example is a membrane-bound heme protein: human or yeast cytochrome b5. It is a bitopic protein having a large globular water-soluble domain containing the heme and a small hydrophobic domain allowing anchoring to microsomal membranes.

All the nucleotide and amino acid sequences are included in the sequence listing.

The amino acid sequence of the human and yeast forms are referred to as follows:

Amino Acid Sequence of Membrane-Bound Human Cytochrome b5 (SEQ ID No. 1)

```
  1 MLAEQSDEAV KYYTLEEIQK HNHSKSTWLI LHHKVYDLTK FLEEHPGGEE VLREQAGGDA
 61 TENFEDVGHS TDAREMSKTF IIGELHPDDR PKLNKPPETL ITTIDSSSSW WTNWVIPAIS
121 AVAVALMYRL YMAED
```

Amino Acid Sequence of Membrane-Bound Yeast Cytochrome b5 (SEQ ID No. 2)

```
  1 MPKVYSYQEV AEHNGPQNFW IIIDDKVYDV SQFKDEHPGG DEIIMDLGGQ DATESFVDIG
 61 HSDEALRLLK GLYIGDVDKT SERVSVEKVS TSENQSKGSG TLVVILAILM LGVAYYLLNE
```

The first experiment to modify the sequences of cytochrome b5 consisted in the removal, on the carboxy-terminal side, of the amino acids involved in the membrane insertion, so as to replace them with four histidines.

This chimeric or fusion protein is obtained by cloning the nucleotide sequence by polymerase chain reaction (PCR).

The cloning kit used is TOPO TA cloning® from Invitrogen. The coding DNA sequence for the chimeric protein is introduced into a pCR®2.1-TOPO® vector. The assembly was amplified in Vial of One Shot® cells. The coding DNA sequence was then transferred into the PUHE25-2 expression vector (SphI cloning for the ATG and Bam HI for the stop).

The base modification for Hb5 is therefore as follows:

Nucleotide Sequence of Membrane-Bound Hb5 (SEQ ID No. 3)

```
  1 ATGGCAGAGC AGTCGGACGA GGCCGTGAAG TACTACACCC TAGAGGAGAT TCAGAAGCAC
 61 AACCACAGCA AGAGCACCTG GCTGATCCTG CACCACAAGG TGTACGATTT GACCAAATTT
121 CTGGAAGAGC ATCCTGGTGG GGAAGAAGTT TTAAGGGAAC AAGCTGGAGG TGACGCTACT
181 GAGAACTTTG AGGATGTCGG GCACTCTACA GATGCCAGGG AAATGTCCAA AACATTCATC
241 ATTGGGGAGC TCCATCCAGA TGACAGACCA AAGTTAAACA AGCCTCCGGA AACTCTTATC
301 ACTACTATTG ATTCTAGTTC CAGTTGGTGG ACCAACTGGG TGATCCCTGC CATCTCTGCA
361 GTGGCCGTCG CCTTGATGTA TCGCCTATAC ATGGCAGAGG ACTGA
```

Nucleotide Sequence of Soluble Hb5-Histidine Tag [Hb5-(His)$_4$] (SEQ ID No. 4)

```
  1 ATGGCAGAGC AGTCGGACGA GGCCGTGAAG TACTACACCC TAGAGGAGAT TCAGAAGCAC
 61 AACCACAGCA AGAGCACCTG GCTGATCCTG CACCACAAGG TGTACGATTT GACCAAATTT
121 CTGGAAGAGC ATCCTGGTGG GGAAGAAGTT TTAAGGGAAC AAGCTGGAGG TGACGCTACT
181 GAGAACTTTG AGGATGTCGG GCACTCTACA GATGCCAGGG AAATGTCCAG AACATTCATC
241 ATTGGGGAGC TCCATCCAGA TGACAGACCA AAGTTAAACA AGCCTCCGGA AACTCTTATC
301 ACTACTATTG ATTCTAGTTC CAGTAACGGA CATCACCACC ATTAA
```

Amino Acid Sequence of [Hb5-(His)₄] (SEQ ID No. 5)

```
  1 MLAEQSDEAV KYYTLEEIQK HNHSKSTWLI LHHKVYDLTK FLEEHPGGEE VLREQAGGDA
 61 TENFEDVGHS TDAREMSRTF IIGELHPDDR PKLNKPPETL ITTIDSSSSN GHHHH
```

2.2) The Water-Soluble Protein-Histidine Tag with a Ser24→Cys mutation

The chimeric protein obtained previously is then mutated in order to reveal a thiol group at the periphery of the protein, via a cysteine residue. This modification is produced by virtue of a site-directed mutagenesis on serine No. 24 of Hb5(His)4.

The mutagenesis kit used is the QuikChange® site-directed Mutagenesis Kit from Stratagene. The action of the pfu DNA polymerase makes it possible to reconstitute the expression vector and the sequence to be mutated. Supercompetent epicurian® XL1-blue bacteria are transformed with this plasmid.

Several different locations for the mutation were tried, and position 24 is in particular exemplified, i.e. a modification of the serine residue to cysteine.

The mutation was verified by sequencing in the laboratory (ABI sequencer):

Nucleotide Sequence of Hb5-(His)₄ mut24 (SEQ ID No. 6)

An agarose gel functionalized with iminodiacetic acid (Sigma) is pre-loaded (flow of 1 ml/min) with nickel by loading a 50 mM solution of nickel chloride solubilized in an acetate buffer, pH 5.4. The column is washed with this same buffer at the same flow and the acetate is then replaced with a 50 mM sodium phosphate buffer, pH 7.

The cell fractionation is directly injected onto the agarose gel column at 5 ml/min. Specifically, the chimeric proteins are retained on the column according to the MIAC technique. The column is subjected to a washing phase with phosphate buffer of increasing concentration of 50 to 250 mM, pH 7, until the solution passing through no longer exhibits an absorption spectrum in the ultraviolet range (240-300 nm). The protein sample is eluted during pulses of histines in solution at a concentration of 1 mg/ml in the 50 mM phosphate buffer, pH 7.

Similar experiments were carried out on the yeast form of cytochrome b5. Thus, it is possible to obtain several mutant

```
  1 ATGGCAGAGC AGTCGGACGA GGCCGTGAAG TACTACACCC TAGAGGAGAT TCAGAAGCAC
 61 AACCACTGCA AGAGCACCTG GCTGATCCTG CACCACAAGG TGTACGATTT GACCAAATTT
121 CTGGAAGAGC ATCCTGGTGG GGAAGAAGTT TTAAGGGAAC AAGCTGGAGG TGACGCTACT
181 GAGAACTTTG AGGATGTCGG GCACTCTACA GATGCCAGGG AAATGTCCAG AACATTCATC
241 ATTGGGGAGC TCCATCCAGA TGACAGACCA AAGTTAAACA AGCCTCCGGA AACTCTTATC
301 ACTACTATTG ATTCTAGTTC CAGTAACGGA CATCACCACC ATTAA
```

Amino Acid Sequence of Hb5-(His)₄ mut24 (SEQ ID No. 7)

```
  1 MLAEQSDEAV KYYTLEEIQK HNHCKSTWLI LHHKVYDLTK FLEEHPGGEE VLREQAGGDA
 61 TENFEDVGHS TDAREMSRTF IIGELHPDDR PKLNKPPETL ITTIDSSSSN GHHHH
```

2.3) Protein Expression in *Escherichia Coli*

The bacterial expression strain is XL1-blue.

A preculture (6 h at 37° C. in 50 ml of medium) of a clone in a Luria-Bertami (LB) medium in the presence of a selection marker, ampicillin, made it possible to seed, in a proportion of 1/100, one liter of Terrific Broth medium supplemented with 100 mg/l of ampicillin.

The culture is placed at ambient temperature with shaking for 48 h and then overexpression of protein is induced by adding isopropyl-β-D-thiogalactopyranoside (IPTG) in a final proportion of 0.5 mM.

2.4) Protein Purification

The bacteria are centrifuged after induction for 24-48 h and are frozen.

A freezing/thawing cycle is followed by a lysis/fractionation step (lysozyme, cholic acid and ultrasonic disintegrator).

The metal ion affinity chromatography (MIAC) purification procedure is defined as follows:

human and yeast chimeric proteins with a high degree of purity and in a proportion of several milligrams of protein.

Example 3

Production of the Floating Protein Anchoring

The hybrid bilayer structure presented in paragraph 1.3 was functionalized with the aim of conferring on the model metal ion affinity properties. To do this, a synthetic phospholipid having an imino-diacetate residue which complexes a nickel divalent cation was chosen. It is DOGS, or 1,2-dioleoyl-sn-glycero-3-[(N-(5-amino-1-carboxypentyl) iminodiacetic acid)succinyl] from Avanti polar Lipid, Inc.

It has been demonstrated that such a molecule allows the interaction of proteins having a polyhistidine domain in their primary sequence. With the aim of introducing these synthetic phospholipids into the membrane model, we produced lipid vesicles composed of a mixture of lipids containing 10% (mol/mol) of modified lipid. These mixed liposomes have the same behavior with respect to the hydrophobic support as those composed of a single species of phospholipids. The fusion results by SPR give rise to values which are comparable in terms of kinetics of fusion and of covering (results not shown).

A method for addressing soluble proteins to membrane supports in a stable and specific manner is to use the coupling between a chelating divalent metal cation present at the surface of the membrane and histidine residues. It has been demonstrated that cytochrome b5 in which the membrane domain has been deleted in favor of a histidine Tag segment conserves an affinity for biological membranes displaying chelating divalent cations.

Various forms of cytochrome b5 with a HisTag domain were produced (paragraph 2.1).

The immobilization of the cytochromes b5 on the hybrid bilayer via an MIAC approach was characterized by SPR (FIG. 2). To evaluate the binding capacity of the membrane, multiple protein injections were performed within its surroundings. The protein concentrations are conventionally between 0.5 and 2 µM and produce biosensor saturation kinetics. For the Hb5(His)4 form, a maximum load signal of 650 RU, which corresponds to approximately 75% of optimum covering on such a membrane model (FIG. 1a), was obtained.

To demonstrate the specific interaction of these proteins with the biosensor, multiple injections of an agent which competes with histidine-Ni2+ coordinations were performed. A solution of histidine at 1 mg/ml injected at the surface of the biosensor produces a large decrease in the signal, i.e. in the amount of cytochrome b5 attached to the membrane (FIG. 2b). In this way, it is possible to compete with the specific interaction and to return to the signal base line.

This procedure, using an aqueous solution which is non-denaturing for the biomolecules, thus enables complete regeneration of the surface of the lipid monolayer.

The results given in FIG. 2 confirm the strong potential of the biosensor in terms of protein capture with a high degree of compactness. They make it possible to underline the very high level of control of the authors over the various phases of construction of this supramolecular assembly since, by modulating the protein or competitor injection pulses, it is possible to precisely attach the amount of protein at the surface.

This great modularity can be summarized in FIG. 3.

Example 4

Protein-ssDNA Grafting Via a Cis-Pt Complex

Platinum complexes, in particular cis-diamine-dichloro-platinums (cis-[PtCl$_2$(NH$_3$)$_2$]) are agents which bind covalently to DNA. In addition, these molecules, by substitution of their labile chloro ligand, can couple, firstly, a base of a DNA and, secondly, a nucleophilic residue of an amino acid of a protein.

4.1) Materials

Cis-[PtCl$_2$(NH$_3$)$_2$] and trans-[PtCl$_2$ (NH$_3$)$_2$] are provided by Johnson Matthey (London, United Kingdom). Cis-[Pt (NH$_3$)$_2$ (H$_2$O)$_2$]$^{2+}$ and trans-[Pt(NH$_3$)$_2$ (H$_2$O)$_2$]$^{2+}$ are prepared by dissolving a suspension of cis-[Pt(NO$_3$)$_2$ (NH$_3$)$_2$] and trans-[Pt(NO$_3$)$_2$ (NH$_3$)$_2$] in water, respectively formed by reacting cis-[PtCl$_2$(NH$_3$)$_2$] and trans-[PtCl$_2$(NH$_3$)$_2$] with silver nitrate.

The 20-mer DNA, its complementary strand and its biotinylated complementary strand come from Eurogentec. The sequence of the 20-mer DNA, 5'CTATCATTTGCT-TACTATTC 3' (SEQ ID No. 13), is chosen such that it possesses only one guanine since the N7 nitrogen is the main site of platination of DNA (Lepre et al., 1990).

4.2) Formation of the DNA-b5 Bridging Via Platinum Bridging

The platination reactions are carried out firstly on the DNA or on the cytochrome b5 (Hb5(His)4 and Hb5(His) 4mut24), but the DNA-b5 bridging yield is greater when the cytochrome b5 is platinated first. Platination of the ssDNA (500 µM) with one equivalent of platinum complex in 70 mM NaClO$_4$ leads to the formation of the cis- or trans-[Pt (NH$_3$)$_2$(H$_2$O)]$^{2+}$ monoadduct linked to the guanine.

The platination site is determined after treatment of the modified oligonucleotide with piperidine-DMS under "Maxam-Gilbert" sequencing conditions followed by treatment with NaCN. A lack of reactivity of the platinated N7 guanine with the dimethyl sulfate (DMS) makes it possible to conclude that the latter is protected with respect to the DMS and is therefore effectively platinated (Comess et al., 1990). The cytochrome b5 (100-200 µM) is incubated in the presence of 5 equivalents of platinum complexes in unbuffered water (pH 5) for 5 hours at 25° C. The cytochrome b5 is then incubated (90 µM) with 1.5 equivalents of DNA in unbuffered water (pH 5) for 50 hours at 25° C. The DNA-b5 complexes are separated from the non-complexed DNA molecules using an agarose gel functionalized with Ni$^{2+}$/iminodiacetic acid groups (Sigma). The protein is eluted by injection of imidazole (1 M). The excess DNA is not retained on the column. The DNA-b5 complexes coupled via a platinum bridge are also purified from the nonreactive forms of DNA using streptavidin-coated magnetic spheres from Promega, according to a modification of the procedure described by Promega: 0.5 nmol of total DNA (complexed or non-complexed) of the complexation mixture is heated at 45° C. for 10 min in water and is then brought into contact with its biotinylated complementary strand in 0.075 M NaCl, 0.0075 M citrate, pH 7.2, at 2.5° C. The mixture (500 µl) is added to 0.6 mg of magnetic spheres complexed with streptavidin, pre-washed and equilibrated in the same buffer at 2.5° C. The ssDNA-b5 platinum complexes are not retained on the spheres and the non-complexed ssDNA is eluted between 30-40° C. in 0.015 M NaCl and 0.0015 M citrate, pH 7.2. These purification steps are followed, firstly, by detection of the radioactivity of the ssDNA labeled with $^{32}$P in the 5' position (radiolabeled beforehand via the action of polynucleotide kinase using [γ$^{32}$P]ATP) and, secondly, by a spectral study over a window of absorbance comprising 413 nm for the b5 (e=100000 M$^{-1}$.cm$^{-1}$) and 260 nm for the ssDNA (e=180500 M$^{-1}$.cm$^{-1}$). The latter is corrected for the Hb5 absorbance component at this wavelength (i.e. ⅕ of its absorbance at 413 nm). However, it is specified that these last two procedures do not make it possible to separate the "ssDNA-b5" platinum complex from the non-complexed cytochrome b5.

The cis-[Pt(NH$_3$)$_2$(H$_2$O)$_2$]$^{2+}$ and trans-[Pt(NH$_3$)$_2$ (H$_2$O)$_2$]$^{2+}$ platinum complexes are capable of coupling the cytochrome b5 with the 20-mer ssDNA. The platination site on the DNA oligonucleotide occurs at N7 of a unique guanine. The "DNA-b5" macromolecular complexes are characterized by gel electrophoresis analyses under denaturing conditions, spectro-photometric quantification analyses and determination of melting temperature with a complementary free ssDNA. An electrophoretic study on SDS-15% PAGE of the mixture composed of the 5'-radiolabeled ssDNA, of Hb5[His]4 and of cis- or trans-[Pt(NH$_3$)$_2$ (H$_2$O)$_2$]$^{2+}$ was carried out.

After migration of the samples, the radioactivity of the ssDNA is associated with the Hb5[His]4 migration band (revealed by coomassie blue staining), demonstrating that a covalent bond has been formed between the 20-mer ssDNA and the cytochrome b5 (FIG. 4). The "DNA-pt-b5" complex was characterized by spectral analysis with the aim of determining the stoichiometry of the reaction between the cytochrome b5 and the 20-mer ssDNA. The experimental conditions allow the formation of an equimolecular complex as indicated by the respective absorbance of the cytochrome b5 at 413 nm and of the 20-mer ssDNA at 260 nm (FIG. 5).

4.3) Determination of the Melting Temperature

The melting temperatures of the 20-mer ssDNA and of the 20-mer ssDNA coupled to the b5 via a cis-$[Pt(NH_3)_2(H_2O)_2]^{2+}$ bridge were determined in 0.1 M $NaClO_4$, pH 4, with their complementary ssDNAs.

The melting temperatures were measured on a Uvikon 941 spectrophotometer (Kontron). 0.2 nmol of 20-mer ssDNA (or "ssDNA-b5-Pt" complex) were incubated with an ssDNA having a complementary sequence, at a final concentration of 0.5 µM, in 0.025 M $NaClO_4$, pH 4.4. The duplex sample is heated to 80° C. (20-mer DNA) or 65° C. ("DNA-Pt-b5"), the temperature is subjected to a decrease of 1° C./min down to 2.5° C., and the absorbance is measured at 260 nm. The samples are heated from 2.5° C. to 60° C. at 1° C./min and their absorbance is followed at 260 nm, with the aim of verifying that the curves obtained during the cooling and the heating can be superimposed (reversible profiles). The Tm values were determined using Kontron software. The melting temperature of the duplex containing the 20-mer ssDNA decreases by 22° C. (from 45° C. to 23° C.) when it is coupled with the cytochrome b5 (FIG. 6).

No difference was observed between the complex comprising Hb5(His)4 and the cysteine mutant; the cysteine at position 24 does not appear, for the cis-Pt complex, to be more reactive than the other nucleophilic sites present at the periphery of the cytochrome b5.

Be that as it may, the platination reactions do not occur on the 4-histidine tag in the carboxy-terminal position, in which case the complex thus formed could not be purified on an agarose-imino-diacetate column or would not be capable of interacting strongly with the cell.

Experiments for characterizing the various complexes by mass spectroscopy (electrospray, Maldi-TOF) are in the process of being carried out.

Example 5

Protein-ssDNA Grafting Via a Spacer Arm 5.1) Functionalization of ssDNA with DPDPB A second alternative was explored, concerning the grafting of a nucleic acid with the cytochrome b5. With a view to optimum display of the DNA coupled at the surface of the membrane biosensor, the inventors chose to use not direct coupling, but preferentially complexation via a spacer arm. The molecule providing the intermolecular bridging is 1,4-di-[3'-(2'-pyridyl-dithio)propionamido]butane, or DPDPB. This molecule allows bonding of the covalent type between two molecules having thiol functions and provides an intermolecular space of 1.6 nm.

In order to produce such a supramolecular assembly, a thiol function was created both on an oligonucleotide and on the cytochrome b5. The modified oligonucleotides are of HPLC quality and are produced by Eurogentec.

The various modified oligonucleotides are as follows:
Oligonucleotide No. W1 (SEQ ID No. 8)

5'GCT-AGC-TGC-ATA-GAT-CTC-TAC-C-SH3'

The thiol modification is performed at the 3' end of the 22-mer.
Oligonucleotide No. W2 (SEQ ID No. 9)

5'GCT-AGC-TGC-ATA-GAT-CTC-TAC-C3'

The thiol modification is performed intra-chain on a thymine placed at position 11 of the 22-mer. The various nonmodified oligonucleotides involved in the exemplification are as follows:
Oligonucleotide No. W3 (SEQ ID No. 10)

5'GGT-AGA-GAT-CTA-TGC-AGC-TAG-G-3'

W3 is the 22-mer complementary to W1.
Oligonucleotide No. W4 (SEQ ID No. 11)

5'-GCA-GCT-AGC-GGT-AGA-GAT-CT-3'

W4 has a sequence complementary to the first 9 bases of W1 (5' side) and to the first 11 bases of W1 (3' side). In this manner, W4 has the particularity of being able to bridge two W1 oligonucleotides.
Oligonucleotide No. W5 (SEQ ID No. 12)

5'-GCT-AGC-TGC-ATA-GAT-CTC-TAC-C-3'

W5 corresponds to the random base sequence of W1.

The DPDPB-W1 coupling procedure is as follows: in order to prevent the dimerization of the W1s by disulfide bonding, the oligonucleotides are treated with a dithiothreitol (DTT) reducing agent, in a molar fraction proportion of ⅕. The mixture is incubated at 30° C. for 15 min. The stock solution of DPDPB is solubilized in dimethyl sulfoxide (DMSO) in a proportion of 10 mg/ml. DPDPB, in a proportion of 1 mol of W1 per 500 to 5 000 mol of DPDPB, is added in the presence of the residual DTT, for an incubation time of 2 to 4 hours at 30° C. The W1 sample is then specifically attached to a DEAE ion exchange column, the reagents are eliminated, and the oligonucleotide is eluted by adding a 1.5 M NaCl solution. The degree of modification can be calculated by assaying the cross-linking agent with DTT. This reduction causes the second thiopyridine group of the bridging agent to leave, and it can be quantified spectrally at 341 nm. The procedure described makes it possible to achieve 100% of complex.

5.2) Cytochrome b5-W1 Grafting Via the Spacer Arm

In order to perform controlled and reversible grafting on the cytochrome b5, the inventors carried out a site-directed mutagenesis of Hb5(His)4 as described in paragraph 2.2, producing the protein Hb5(His)4mutant24. The serine→cysteine mutation makes it possible to specifically introduce a thiol group at the periphery of the protein. In order to prevent dimerization of the proteins, the solution is treated with DTT (Xmol b5/DTT=⅕) for 30 min at 30° C. The sample is then loaded onto a gel exclusion chromatography column (G25) so as to remove the DTT and is immediately injected into the solution of modified oligonucleotides (Xmol b5/W1=½) for 4 h at 30° C. The excess oligonucleotide is removed by retention of the proteins on an iminodiacetate-$Ni^{2+}$gel. Elution of the proteins is obtained by pulses of a 1 mg/ml histidine solution, as indicated during the HisTag protein purification step. Spectral analysis over a [240-500] nm window makes it possible to demonstrate the effective coupling of Hb5(His)4mut24 with W1 (FIG. 7).

With regard to the molar absorption coefficients of the two macromolecules, the degrees of complexation range from 35 to 65%.

In order to subsequently use only an equimolecular Hb5/W1 population, an additional purification step is carried out on DEAE. Elution performed under an NaCl concentration gradient makes it possible to isolate the various species reconstituted during the coupling (monomeric and dimeric Hb5, Hb5-spacer-W1). Thus, all the species are separated from the initial population, by an increasing NaCl gradient (FIG. 7):

Spectrum a) Hb5(His)4mut24 monomer
Spectrum b) Hb5(His)4mut24 dimer
Spectrum c) equimolar b5-W1 complex.

According to this procedure, the b5-W1 population is isolated and can be brought into contact with the hybrid membrane.

Example 6

Preparation of the Supramolecular Assembly "b5-cis Pt-ssDNA" and "b5-DPDPB-ssDNA"

The grafting of the various complexes onto the hybrid bilayer was characterized by surface plasmon resonance in a BIAcore device. Radioactivity-based and fluorescence labeling-based experiments are in the process of being developed in the laboratory.

The experiments consisting of coupling the molecular assembly to the lipid model by virtue of the chelating nickel complex by surface plasmon resonance made it possible to show the formation of a stable complex.

The levels of compactness obtained with the assembly appear, on the other hand, to be less than those obtained with the protein not modified with the oligonucleotide. The increase in negative charges introduced by W1 may be responsible for repulsions between supramolecular blocks and may thus lead to less covering. The covering values were evaluated at between 200 and 250 RU.

It was verified that, like Hb5(His)4, the structures are interacting specifically with the support and that the action of agents which compete with the chelation, such as a 1 mg/ml histidine solution, allows complete regeneration of the structure (data not shown, but exhibiting the same behavior as those appearing in FIG. 2).

Example 7

Potential of the Biosensor and Detection of Hybridization

In order to evaluate the potential of the membrane biosensor in terms of specificity and sensitivity, various tests were carried out.

Firstly, it was essential to verify the absence of nonspecific interactions of oligonucleotides with the biosensor. To do this, various injections of W4 were performed. W4 represents a random sequence from the bases constituting W1; studying the evolution of the signal made it possible to show that W4 does not interact at the surface of the biosensor, i.e. the lipid structure and the b5-W1 supramolecular assembly, whatever the bridging means (cis-Pt or DPDPB).

Secondly, various injections of W3 were performed at various salt concentrations. Thus, it was clearly demonstrated that the injections of W3, the sequence complementary to W1, in the presence of a high concentration of NaCl were accompanied by association or hybridization kinetics. On the other hand, for concentrations of NaCl less than or equal to 20 mM, the same oligonucleotide interacts very little or not at all with the biosensor.

These results demonstrate the possibility of detecting hybridization states between two ssDNAs at the surface of the biosensor. The hybridization results show a threshold value of approximately 30 to 35 RU. Now, according to the various methods of calibration, the value expected for complete hybridization based on a b5-W1 block signal of 250 RU is 70 RU. However, the Tm measurements made on W1 clearly show a phase transition temperature close to ambient temperature, i.e. the temperature at which measurements are made in the BIAcore device. At this temperature, only 50% of the hybridization is expected. The value measured with our device is therefore close to optimum hybridization, which is proof of a very favorable accessibility of the target molecules displayed by the biosensor.

The size of the working cell within the BIAcore device is of the order of 1 $mm^2$. However, the surface really probed by the damped wave represents only 0.224 $mm^2$. Considering the calibration 1000 RU$\leftarrow\rightarrow$0.224 ng/0.224 $mm^2$, 250 RU of molecular assembly correspond to 0.1 ng, i.e. 5 fmol $\approx 3\times 10^9$ molecules. The membrane biosensor allows the molecular hybridization of approximately $10^9$ molecules.

In addition, the biosensor presented requires only the capture of a complementary ssDNA, without it being necessary to use a labeled probe.

BIBLIOGRAPHICAL REFERENCES

Berney et al. (2000) Sensors amd Actuators B 68, 100-108
Boncheva et al. (1999) Langmuir 15, 4317-4320
Boon et al. (2000) Natural Biotechnology 18, 1096-1100
Braun et al. (1998) Nature 391, 775-778
Cheng et al (2000) Reviews in molecular biotechnology 74, 159-174 (p 18)
Comess et al. (1990) Biochemistry, 29, 2102-2110
Ebbesen et al. (1998) Nature 391, 667-669 (p 18)
Gulik-Krzywicki et al. (1967) J Mol Biol; 27(2): 303-22
Heyse et al. (1998) Biochemistry 37, 507-522
Kalb et al. (1992) Biochim. Biophys. Acta 1103: 307-316
Lepre et al. (1990) Nucleic Acids Molec. Biol., 4, 9-38
Marchal et al. (1998) Biophysical Journal 74, 1937-1948
Steel et al. (2000) Biophysical Journal 79, 975-981
Wittung-Stafshede et al. (2000) Colloids and Surfaces 174, 269-273

The invention claimed is:

1. A cell for displaying a nucleic acid, comprising:
a support which is substantially flat on an atomic scale,
a protein III having an unequivocal three-dimensional structure, protein III is chosen from the group consisting of proteins having a redox center and proteins having an anisotropic optical absorption property,
a nucleic acid IV linked to said protein III, the nucleic acid-protein assembly being laterally mobile relative to said support, such that the hybridization of a target nucleic acid to said nucleic acid IV or the change in conformation of said nucleic acid IV can be detected via the geometric reorganization of the nucleic acid-protein assembly.

2. The cell as claimed in claim 1, comprising:
a support which is substantially flat on an atomic scale, to which is attached
a hydrophobic monolayer I, on which is present
a monolayer II comprising phospholipids,
a bridging molecule having a hydrophobic end which can interact with the monolayer II, and an end which is chemically functionalized so as to form a stable bond with a protein III,
a protein III having an unequivocal three-dimensional structure, said protein III being laterally mobile in said layer II,
a nucleic acid TV unequivocally attached to said protein III, preferably via a molecular arm.

3. The cell as claimed in claims 1 or 2, wherein the nucleic acid is attached to said protein via a covalent bond.

4. The cell as claimed in claim 1, wherein the nucleic acid is attached to said protein via a reversible bond.

5. The cell as claimed in claim 1, wherein the nucleic acid IV is attached to said protein III via a compound chosen from:
   a spacer arm connecting two identical or different, chemically reactive residues of the nucleic acid IV and of the protein III, chosen from the group consisting of thiols, amines, amides and arginines;
   a metal complex coordinated, firstly, with an amino residue or a group of amino residues of said protein III and, secondly, with one or more natural or modified bases of the nucleic acid IV,
   a covalent or noncovalent protein complex involving the nucleic acid IV.

6. The cell as claimed in claim 1, wherein said protein III has undergone a modification which introduces a unique site for effecting said bond with said nucleic acid IV in an unequivocal manner.

7. The cell as claimed in claim 6, wherein said modification consists of a mutation of said protein so as to introduce just one unique predetermined amino acid.

8. The cell as claimed in claim 7, wherein said predetermined amino acid is a cysteine.

9. The cell as claimed in claim 2, wherein said protein III is attached to a phospholipid of the layer II.

10. The cell as claimed in claim 9, wherein said protein-phospholipid bond is a covalent bond.

11. The cell as claimed in claim 9, wherein said protein-phospholipid bond is a reversible bond.

12. The cell as claimed in claim 9, wherein said protein III is linked to a modified phospholipid of the layer II, said phospholipid having a chelate-binding zone.

13. The cell as claimed in claim 2, wherein said protein III has a hydrophobic tail which allows it to be anchored in the layer II.

14. The cell as claimed in claim 2, wherein the phospholipids of the layer II have hydrophobic tails chosen such that said layer is not in the crystalline state, but in the fluid state at the temperature for use.

15. The cell as claimed in claim 14, wherein said hydrophobic tails are greater than or equal to 14 carbon atoms in chain length, said chain possibly having unsaturations, such that said layer II is in the fluid state at the temperature for use.

16. The cell as claimed in claim 2, wherein said phospholipids of the layer II have polar heads, chosen from the group consisting of neutral polar heads carrying no charges, polar heads which are neutral overall but which carry opposite charges (zwitterionic polar heads), or polar heads carrying an overall negative charge.

17. The cell as claimed in claim 2, wherein said layer I comprises hydrophobic elements with a chain length of approximately 2 to 2.5 nm.

18. The cell as claimed in claim 16, wherein said layer I comprises phospholipids linked to said support via their polar heads.

19. The cell as claimed in claim 2, wherein said layer I comprises hydrophobic elements linked to said support via a covalent bond.

20. The cell as claimed in claim 1, wherein the flatness of said support is such that the difference in height between two zones separated by less than 100 nm is less than or equal to 10 nm.

21. The cell as claimed in claim 1, wherein said support consists of a material chosen from the group consisting of glass covered with a layer of gold, cleaved mica, silicon or any other monocrystalline material.

22. The cell as claimed in claim 1, wherein it comprises several identical or different proteins linked to identical or different nucleic acids.

23. A support for detecting nucleic acids, displaying a plurality of cells as claimed in claim 1.

24. The support as claimed in claim 23, wherein it comprises a system for measuring current, impedance or potential.

25. The support as claimed in claim 23, wherein it comprises, between each cell, an integrated optical device capable of measuring the absorbance of a cell in two cross directions and of deducing therefrom its state of organization (anisotropy) or of disorganization (isotropy).

26. The support as claimed in claim 23, wherein it comprises a surface alternating conducting and reflecting zones and nonconducting and transparent zones.

27. A method for identifying the presence of a test nucleic acid in a sample, comprising the steps of:
   a) bringing said sample into contact with a cell as claimed in claim 1, under conditions which allow the hybridization of said test nucleic acid to a nucleic acid attached to a protein of said cell,
   b) detecting the hybridization of said test nucleic acid to said nucleic acid attached to said protein.

28. A method for identifying the binding of a protein to a nucleic acid, and/or its activity on the conformation of said nucleic acid, comprising the steps of:
   a) bringing said protein into contact with a nucleic acid attached to a protein, in a cell as claimed in claim 1,
   b) detecting the binding of said protein to said nucleic acid, and/or its activity on the conformation of said nucleic acid.

29. A method for identifying the binding of a ligand to a protein attached to a nucleic acid attached to a protein in a cell as claimed in claim 1, comprising the steps of:
   a) bringing said ligand into contact with said protein,
   b) detecting the binding of said ligand to said protein.

30. A method for identifying the binding of a compound to a nucleic acid, and/or its activity on the conformation of said nucleic acid, comprising the steps of:
   a) bringing said compound into contact with a nucleic acid attached to a protein, in a cell as claimed in claim 1,
   b) detecting the binding of said compound to said nucleic acid, and/or its activity on the conformation of said nucleic acid.

31. The method of identification as claimed in claim 27, wherein the detection is carried out via an optical (absorbance, fluorescence), electrical, electron-based, surface plasmon resonance, energy transfer, radiolabeling, diffraction (optical, electron, X-ray, neutron diffraction) or microscopy (direct optical or fluorescence microscopy, electron microscopy, near-field microscopy, atomic force microscopy) system.

* * * * *

SEQUENCE LISTING

<160> NUMBER OF SEQ ID NOS: 13

<210> SEQ ID NO 1
<211> LENGTH: 135

```
<212> TYPE: PRT
<213> ORGANISM: Homo sapiens
<220> FEATURE:
<223> OTHER INFORMATION: Human membrane b5-Cytochrome

<400> SEQUENCE: 1
```

Met Leu Ala Glu Gln Ser Asp Glu Ala Val Lys Tyr Tyr Thr Leu Glu
 1               5                  10                  15

Glu Ile Gln Lys His Asn His Ser Lys Ser Thr Trp Leu Ile Leu His
            20                  25                  30

His Lys Val Tyr Asp Leu Thr Lys Phe Leu Glu Glu His Pro Gly Gly
        35                  40                  45

Glu Glu Val Leu Arg Glu Gln Ala Gly Gly Asp Ala Thr Glu Asn Phe
    50                  55                  60

Glu Asp Val Gly His Ser Thr Asp Ala Arg Glu Met Ser Lys Thr Phe
65                  70                  75                  80

Ile Ile Gly Glu Leu His Pro Asp Asp Arg Pro Lys Leu Asn Lys Pro
                85                  90                  95

Pro Glu Thr Leu Ile Thr Thr Ile Asp Ser Ser Ser Ser Trp Trp Thr
            100                 105                 110

Asn Trp Val Ile Pro Ala Ile Ser Ala Val Ala Val Ala Leu Met Tyr
        115                 120                 125

Arg Leu Tyr Met Ala Glu Asp
    130                 135

```
<210> SEQ ID NO 2
<211> LENGTH: 120
<212> TYPE: PRT
<213> ORGANISM: Saccharomyces cerevisiae
<220> FEATURE:
<223> OTHER INFORMATION: Yeast membrane b5-Cytochrome

<400> SEQUENCE: 2
```

Met Pro Lys Val Tyr Ser Tyr Gln Glu Val Ala Glu His Asn Gly Pro
 1               5                  10                  15

Gln Asn Phe Trp Ile Ile Ile Asp Asp Lys Val Tyr Asp Val Ser Gln
            20                  25                  30

Phe Lys Asp Glu His Pro Gly Gly Asp Glu Ile Ile Met Asp Leu Gly
        35                  40                  45

Gly Gln Asp Ala Thr Glu Ser Phe Val Asp Ile Gly His Ser Asp Glu
    50                  55                  60

Ala Leu Arg Leu Leu Lys Gly Leu Tyr Ile Gly Asp Val Asp Lys Thr
65                  70                  75                  80

Ser Glu Arg Val Ser Val Glu Lys Val Ser Thr Ser Glu Asn Gln Ser
                85                  90                  95

Lys Gly Ser Gly Thr Leu Val Val Ile Leu Ala Ile Leu Met Leu Gly
            100                 105                 110

Val Ala Tyr Tyr Leu Leu Asn Glu
        115                 120

```
<210> SEQ ID NO 3
<211> LENGTH: 405
<212> TYPE: DNA
<213> ORGANISM: Homo sapiens
<220> FEATURE:
<223> OTHER INFORMATION: Human membrane b5-Cytochrome (Hb5)

<400> SEQUENCE: 3
```
atggcagagc agtcggacga ggccgtgaag tactacaccc tagaggagat tcagaagcac      60

-continued

```
aaccacagca agagcacctg gctgatcctg caccacaagg tgtacgattt gaccaaattt      120
ctggaagagc atcctggtgg ggaagaagtt ttaagggaac aagctggagg tgacgctact      180
gagaactttg aggatgtcgg cactctaca gatgccaggg aaatgtccaa acattcatc       240 attggggagc tccatccaga tgacagacca agttaaaca agcctccgga aactcttatc      300
actactattg attctagttc cagttggtgg accaactggg tgatccctgc catctctgca     360
gtggccgtcg ccttgatgta tcgcctatac atggcagagg actga                    405
```

<210> SEQ ID NO 4
<211> LENGTH: 345
<212> TYPE: DNA
<213> ORGANISM: Artificial sequence
<220> FEATURE:
<223> OTHER INFORMATION: Description of artificial sequence: Human
      cytochrome b5-histidine 4 fusion protein [Hb5-(His)4]

<400> SEQUENCE: 4

```
atggcagagc agtcggacga ggccgtgaag tactacaccc tagaggagat tcagaagcac       60
aaccacagca agagcacctg gctgatcctg caccacaagg tgtacgattt gaccaaattt      120
ctggaagagc atcctggtgg ggaagaagtt ttaagggaac aagctggagg tgacgctact      180
gagaactttg aggatgtcgg cactctaca gatgccaggg aaatgtccag acattcatc       240 attggggagc tccatccaga tgacagacca agttaaaca agcctccgga aactcttatc      300
actactattg attctagttc cagtaacgga catcaccacc attaa                     345
```

<210> SEQ ID NO 5
<211> LENGTH: 115
<212> TYPE: PRT
<213> ORGANISM: Artificial sequence
<220> FEATURE:
<223> OTHER INFORMATION: Description of artificial sequence: Human
      cytochrome b5-histidine 4 fusion protein (Hb5-(His)4).

<400> SEQUENCE: 5

```
Met Leu Ala Glu Gln Ser Asp Glu Ala Val Lys Tyr Tyr Thr Leu Glu
  1               5                  10                  15

Glu Ile Gln Lys His Asn His Ser Lys Ser Thr Trp Leu Ile Leu His
             20                  25                  30

His Lys Val Tyr Asp Leu Thr Lys Phe Leu Glu Glu His Pro Gly Gly
         35                  40                  45

Glu Glu Val Leu Arg Glu Gln Ala Gly Gly Asp Ala Thr Glu Asn Phe
     50                  55                  60

Glu Asp Val Gly His Ser Thr Asp Ala Arg Glu Met Ser Arg Thr Phe
 65                  70                  75                  80

Ile Ile Gly Glu Leu His Pro Asp Asp Arg Pro Lys Leu Asn Lys Pro
                 85                  90                  95

Pro Glu Thr Leu Ile Thr Thr Ile Asp Ser Ser Ser Ser Asn Gly His
            100                 105                 110

His His His
        115
```

<210> SEQ ID NO 6
<211> LENGTH: 345
<212> TYPE: DNA
<213> ORGANISM: Artificial sequence
<220> FEATURE:
<223> OTHER INFORMATION: Description of artificial sequence: Cysteine
      (position 24) mutant of human     cytochrome b5-histidine 4
      fusion prote -continued

<400> SEQUENCE: 6

```
atggcagagc agtcggacga ggccgtgaag tactacaccc tagaggagat tcagaagcac    60
aaccactgca agagcacctg gctgatcctg caccacaagg tgtacgattt gaccaaattt   120
ctggaagagc atcctggtgg ggaagaagtt ttaagggaac aagctggagg tgacgctact   180
gagaactttg aggatgtcgg gcactctaca gatgccaggg aaatgtccag aacattcatc   240
attggggagc tccatccaga tgacagacca aagttaaaca agcctccgga aactcttatc   300
actactattg attctagttc cagtaacgga catcaccacc attaa                   345
```

<210> SEQ ID NO 7
<211> LENGTH: 115
<212> TYPE: PRT
<213> ORGANISM: Artificial sequence
<220> FEATURE:
<223> OTHER INFORMATION: Description of artificial sequence: Cysteine
      (position 24) mutant of human      cytochrome b5-histidine 4
      fusion prote

<400> SEQUENCE: 7

```
Met Leu Ala Glu Gln Ser Asp Glu Ala Val Lys Tyr Tyr Thr Leu Glu
  1               5                  10                  15

Glu Ile Gln Lys His Asn His Cys Lys Ser Thr Trp Leu Ile Leu His
             20                  25                  30

His Lys Val Tyr Asp Leu Thr Lys Phe Leu Glu Glu His Pro Gly Gly
         35                  40                  45

Glu Glu Val Leu Arg Glu Gln Ala Gly Gly Asp Ala Thr Glu Asn Phe
     50                  55                  60

Glu Asp Val Gly His Ser Thr Asp Ala Arg Glu Met Ser Arg Thr Phe
 65                  70                  75                  80

Ile Ile Gly Glu Leu His Pro Asp Asp Arg Pro Lys Leu Asn Lys Pro
                 85                  90                  95

Pro Glu Thr Leu Ile Thr Thr Ile Asp Ser Ser Ser Ser Asn Gly His
            100                 105                 110

His His His
        115
```

<210> SEQ ID NO 8
<211> LENGTH: 22
<212> TYPE: DNA
<213> ORGANISM: Artificial sequence
<220> FEATURE:
<221> NAME/KEY: modified_base
<222> LOCATION: (22)..(22)
<223> OTHER INFORMATION: /mod_base=Cysteine
      /note="thiol fixed on C"
<220> FEATURE:
<223> OTHER INFORMATION: Description of artificial sequence:
      Oligonucleotide n0W1

<400> SEQUENCE: 8

```
gctagctgca tagatctcta cc                                             22
```

<210> SEQ ID NO 9
<211> LENGTH: 22
<212> TYPE: DNA
<213> ORGANISM: Artificial sequence
<220> FEATURE:
<221> NAME/KEY: modified_base
<222> LOCATION: (11)..(11)
<223> OTHER INFORMATION: /mod_base=thymine
      /note="Thiol modification on T"

-continued

```
<220> FEATURE:
<223> OTHER INFORMATION: Description of artificial sequence:
      Oligonucleotide n0W2

<400> SEQUENCE: 9
gctagctgca tagatctcta cc                                               22

<210> SEQ ID NO 10
<211> LENGTH: 22
<212> TYPE: DNA
<213> ORGANISM: Artificial sequence
<220> FEATURE:
<223> OTHER INFORMATION: W3 complementary of W1
<220> FEATURE:
<223> OTHER INFORMATION: Description of artificial sequence:
      Oligonucleotide No.W3

<400> SEQUENCE: 10
ggtagagatc tatgcagcta gg                                               22

<210> SEQ ID NO 11
<211> LENGTH: 20
<212> TYPE: DNA
<213> ORGANISM: Artificial sequence
<220> FEATURE:
<223> OTHER INFORMATION: Complementary sequence of first 9 bases of
      W1 (5' end) and of first 11 bases of W1 (3' end)
<220> FEATURE:
<223> OTHER INFORMATION: Description of artificial sequence:
      Oligonucleotide No. W4

<400> SEQUENCE: 11
gcagctagcg gtagagatct                                                  20

<210> SEQ ID NO 12
<211> LENGTH: 22
<212> TYPE: DNA
<213> ORGANISM: Artificial sequence
<220> FEATURE:
<223> OTHER INFORMATION: Random sequence of W1
<220> FEATURE:
<223> OTHER INFORMATION: Description of artificial sequence:
      Oligonucleotide No. W5

<400> SEQUENCE: 12
gctagctgca tagatctcta cc                                               22

<210> SEQ ID NO 13
<211> LENGTH: 20
<212> TYPE: DNA
<213> ORGANISM: Artificial sequence
<220> FEATURE:
<221> NAME/KEY: modified_base
<222> LOCATION: (10)..(10)
<223> OTHER INFORMATION: /mod_base=guanine
      /note="Platine set on G"
<220> FEATURE:
<223> OTHER INFORMATION: Description of artificial sequence: 20-mer DNA
      sequence chosen for containing only one guanine.

<400> SEQUENCE: 13
ctatcatttg cttactattc                                                  20
```